(12) United States Patent
Gwathmey

(10) Patent No.: US 8,029,795 B2
(45) Date of Patent: Oct. 4, 2011

(54) TARGETED IRON CHELATOR DELIVERY SYSTEM

(75) Inventor: Judith K. Gwathmey, Cambridge, MA (US)

(73) Assignee: Gwathmey, Inc., Cambridge, MA (US)

( * ) Notice: Subject to any disclaimer, the term of this patent is extended or adjusted under 35 U.S.C. 154(b) by 339 days.

(21) Appl. No.: 11/011,750

(22) Filed: Dec. 14, 2004

(65) Prior Publication Data

US 2005/0175684 A1 Aug. 11, 2005

Related U.S. Application Data

(63) Continuation-in-part of application No. 09/751,769, filed on Dec. 29, 2000, now Pat. No. 6,960,560.

(60) Provisional application No. 60/173,924, filed on Dec. 30, 1999.

(51) Int. Cl.
*A61K 9/127* (2006.01)
*A61K 39/395* (2006.01)
*A61K 51/12* (2006.01)

(52) U.S. Cl. ............... 424/152.1; 424/1.21; 424/450; 424/489; 424/490; 424/172.1; 424/178.1

(58) Field of Classification Search ............ 424/1.21, 424/450, 489, 490, 152.1, 172.1, 178.1; 436/529
See application file for complete search history.

(56) References Cited

U.S. PATENT DOCUMENTS

| | | | | |
|---|---|---|---|---|
| 4,397,867 A | * | 8/1983 | Blake | 514/575 |
| 6,056,938 A | * | 5/2000 | Unger et al. | 424/1.21 |
| 7,494,666 B2 | * | 2/2009 | McDonald et al. | 424/450 |
| 2001/0048914 A1 | * | 12/2001 | Larsen et al. | 424/1.41 |
| 2002/0028474 A1 | * | 3/2002 | Shibamura et al. | 435/7.23 |

FOREIGN PATENT DOCUMENTS

| WO | WO 01/49266 A2 | | 7/2001 |
|---|---|---|---|
| WO | WO 2004/002455 A1 | * | 1/2004 |

OTHER PUBLICATIONS

Wu et al., "The prospects of hepatic drug delivery and gene therapy," *Expert Opin Investig Drugs*, 7(11), pp. 1795-1817, 1998.
Nag et al., "Assessment of targeting potential of galactosylated and mannosylated sterically stabilized liposomes to different cell types of mouse liver," *J. Drug Target*, 6(6), pp. 427-438, 1999.
Klibanov et al., "Targeting of macromolecular carriers and liposomes by antibodies to myosin heavy chain," *Am. J. Physiol.*, 261(4) Suppl., pp. 60-65, 1991.
Torchillin et al., "Preservation of antimyosin antibody activity after covalent coupling to liposomes," Biochem. Biophys. Res. Commun. 89(4), 1114-1119, 1979.
Dufresne et al., "Targeting lymph nodes with liposomes bearing anti-HLA-DR Fab' fragments," Biochim. Biophys. Acta, 1421(2), 284-294, 1999.
Maruyama et al., "Lipid composition is important for highly efficient target binding and retention of immunoliposomes," Proc. Nat'l. Acad. Sci., USA, 87:5744-5748, 1990.
Maruyama et al., "Possibility of active targeting to tumor tissues with liposomes," Adv. Drug. Deliv. Rev., 40 (1-2), 89-102, 1999.
Vingerhoeds et al., "Immunoliposomes in Vivo," Immunomethods, 4(3), 259-272, 1994.
Hopkins, S.J. et al., "Liposome-Entrapped Desferrioxamine," *Drugs of the Future*, vol. 4, No. 7, pp. 500-506 (1979).
Lau, E.H. et al., Improvement of iron removal from reticuloendothelial system by liposome encapsulation of N,N'-bis[2-hydroxy-benzyl]-ethylenediamine-N,N'-diacetic adic (HBED), *J. Laboratory and Clinical Medicine*, vol. 101, No. 5, pp. 806-816 (1983).
Lau, E.H. et al., "Liposome-encapsulated Desferrioxamine in Experimental Iron Overload," *British J. of Haematology*, vol. 47, pp. 505-518 (1981).
Postma, N.S. et al., "Absorption and biodistribuion of $^{111}$indium-labelled desferrioxamine ($^{111}$In-DFO) after subcutaneous injection of $^{111}$In-DFO liposomes," *J. of Controlled Release*, vol. 58, pp. 51-60 (1999).
Rahman, Y.E., "Liposomes as Delivery Systems for Iron Chelators," *Devel. Of Iron Chelators for Clinical Use*, Proc. Symp., $2^{nd}$, pp. 211-225 (1980).
Rahman, Y.E. et al., "Application of Liposomes to Metal Chelation Therapy," *Liposomes and Immunobiology*, Proc. Nat'l Symp., pp. 285-299 (1980).
Young, S.P. et al., "Liposome Entrapped Desferrioxamine and Iron Transporting Ionophores: a New Approach to Iron Chelation Therapy," *British J. of Haematology*, vol. 41, pp. 357-363 (1979).
Leserman et al., "Targeting to cells of fluorescent liposomes covalently coupled with monoclonal antibody or protein A," Nature, 288:602-604, 1980.
Caride, V.J., "Liposome Accumulation in Regions of Experimental Myocardial Infarction", Science, vol. 198, pp. 735-738, Nov. 18, 1977.

* cited by examiner

*Primary Examiner* — David A Saunders

(74) *Attorney, Agent, or Firm* — Lando & Anastasi LLP

(57) ABSTRACT

A targeted iron chelator delivery system that comprises an iron chelator, a targeting agent and a lipid carrier, e.g., a liposome, is provided. The iron chelator delivery system may be used to remove excess iron from specific organs such as, for example, heart and liver tissue. Methods for preparing and administering the targeted iron chelator delivery system are also provided. The iron chelator delivery system may be administered during a blood transfusion to prevent iron overload.

17 Claims, 32 Drawing Sheets

| Group | Iron | Hepatic Index |
|---|---|---|
| Controls | 190±10 * | 0.1 |
| Overloaded | 2029.5±200 | 2.0 |
| Overloaded +DFO | 1700±200* | 1.8 |
| Overload + Liposomes plus DFO | 1000±50 *ƒ | 1.5 |
| Overload +Liposomes | 2011.8±25 | 1.9 |

*p<0.05 compared to Iron overloaded. ƒ p<0.05 compared to standard DFO treatment.
DFO = Desferrioxamine

FIG. 3

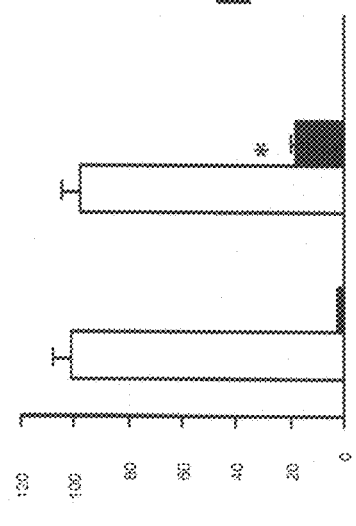
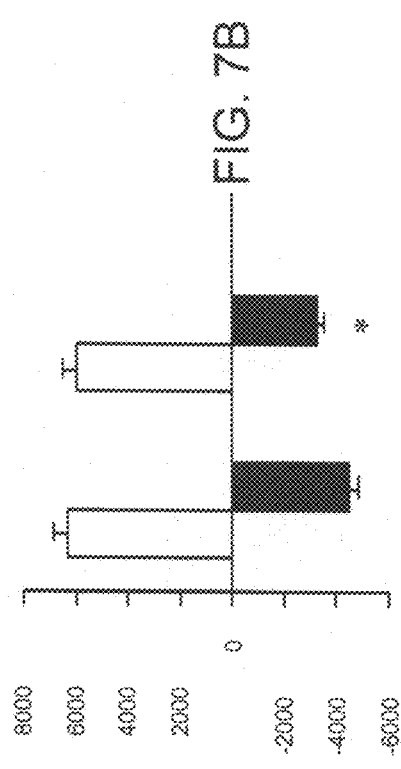
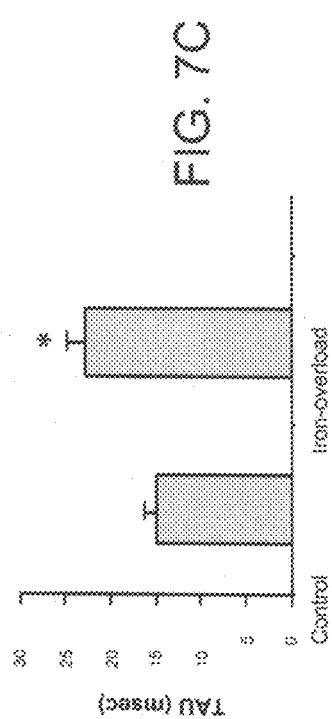
FIG. 7A
FIG. 7B
FIG. 7C

Blood Chemistry Values Before and After Liposome Infusion (with and without DFO)

|          | Before      | 24 hrs after Infusion | 5 days after Infusion |
|----------|-------------|-----------------------|-----------------------|
| SGOT     | 100 ± 10    | 102 ± 10              | 100 ± 10              |
| SGPT     | 36 ± 2      | 36 ± 2                | 37 ± 2                |
| *AP      |             | 97 ± 1                | 97 ± 0.4              |
| BUN      | 17 ± 0.4    | 17 ± 1                | 18 ± 2                |
| Iron (blood) | 205 ± 7 | 203 ± 3               | 205 ± 5               |
| Total CK | 2 ± 0       | 0 ± 0                 | 0 ± 0                 |

*AP = alkaline phosphatase

FIG. 13

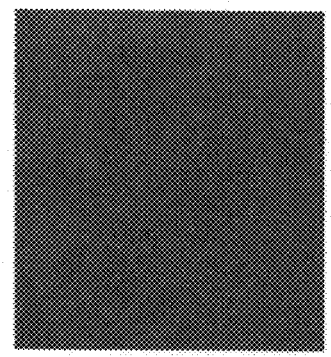
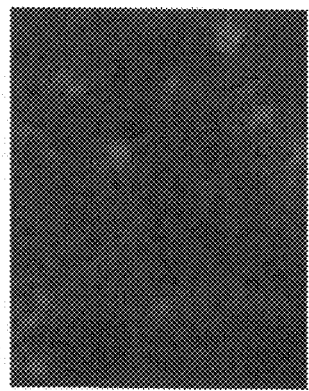
FIG. 29

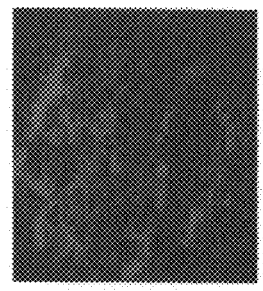
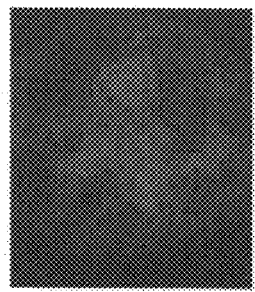
FIG. 30

TARGETED IRON CHELATOR DELIVERY SYSTEM

CROSS-REFERENCE APPLICATION AND PRIORITY CLAIM

This application is a continuation-in-part of U.S. application Ser. No. 09/751,769 entitled "Iron Chelator Delivery System," filed on Dec. 29, 2000, now U.S. Pat. No. 6,960,560, and claims the benefit of U.S. application Ser. No. 60/173,924, filed Dec. 30, 1999, the entire disclosures of which are incorporated herein by reference for all purposes.

FIELD OF THE INVENTION

Certain examples are directed to targeted iron chelator delivery systems for removal of excess iron from targeted cells, tissues or organs, such as, for example, the liver or heart.

BACKGROUND

Iron-overload due to transfusion currently occurs with any patient who receives more than 30 or 40 transfusions over the course of his or her life. The excess iron can injure any organ in the body. The heart and liver are particularly susceptible to damage, and failure of one of these organs is often the cause of death in patients with transfusional iron-overload. Transfusion related iron-overload is a major cause of morbidity and mortality in patients with a variety of transfusion-dependent anemias, hereditary hemochromatosis, including thalassemia major (Cooley's anemia).

Transfusion associated iron-overload develops in conditions characterized by severe, life-threatening anemia where transfusions substantially prolong life expectancy (Cairo, M. (1990) Introduction. Am. J. Pediatr. Hematol. Onco. 12:1-3). The most notable causes of transfusional iron-overload are the thalassemias, mild aplastic anemia, and congenital anemia (McLaren G. M. W. et al. (1983) CRC Crit. Rev. Clin. Lab. Sci. 126:896-899). Children with sickle cell disease and children who are stroke prone with sickle cell disease who receive chronic transfusions for complications may also suffer from iron-overload (Pegelow, C. et al. (1997) J. Pediatr. 126:896-899; Adams, R., et al. (1988) NEJM 339:5-11).

Transfused red cells are engulfed and destroyed at the end of their life span by stationary reticuloendothelial cells in the liver (Kupfer cells) and the spleen. The iron from the hemoglobin is removed and stored as hemosiderin. The reticuloendothelial cells return some of this iron to the circulation coupled to transferrin, and the iron is redistributed to the cells of the body. No known physiological mechanism of iron excretion exists. Therefore, after a number of transfusions, the level of iron in the body reaches a toxic level. At that point, chelation therapy is required. Iron that is stored in hemosiderin is innocuous. This iron is in equilibrium, however, with a very small pool of so-called "free iron" in the cell. This pool of iron is so small that its size has never been satisfactorily determined. Better termed "loosely-bound iron," this material catalyzes the formation of reactive oxygen species through Fenton chemistry. These reactive oxygen species are the agents of cell injury.

Iron-overload, whether due to chronic transfusions or hereditary hemochromotosis, has a plethora of side-effects (Bonkovsky, H. (1991) American Journal of Medical Science 301:32-43), (Koren, A. et al. (1987) Am. J. Dis. Child. 141: 93-96). Liver damage and heart failure are the two most common causes of death. Liver iron deposition initiates hepatic fibrosis, cirrhosis and death (Bonkovsky, H. (1991) American Journal of Medical Science 301:32-43). Congestive heart failure or death from cardiac arrhythmias is common (Koren, A. et al. (1987) Am. J. Dis. Child. 141:93-96). For disorders such as thalassemia major (by definition, transfusion-dependent thalassemia), iron-overload now is the limiting factor in survival. The advent of chronic transfusion therapy in the 1960's increased life span to the early to mid-twenties, however, the pernicious consequences of iron-overload were invariably fatal (Cooley, T. (1945) Am. J. Med. 209:561-572), (Piomelli, S. (1991) Hematol. Oncol. Clin. North. Am. 5:557-569).

Iron is one of the leading causes of pediatric poisoning deaths in the United States (Litovitz, T. L. et al. (1992) Am. J. Emerg. Med. 10:452-505). Numerous reports of serious or fatal poisonings have been cited in the medical literature (Litovitz, T. L. et al. (1992); Westlin, W. F. (1966) Clin. Pediatr. 5:531-535; Henriksson, P. et al. (1979) Scand. J. Haematol. 22:235-240) including five toddler deaths in Los Angeles county during a seven month period in 1992 (Weiss, B. et al. (1993) Morb. Mortal. Wkly. Rep. 42:111-113). It is clear that iron can cause serious morbidity and mortality, yet many clinicians and families remain unaware of the dangers of iron (Anderson, B. D. (Apr. 18, 2000) Medscape Pharmacists). Although uncommon, iron solutions may be absorbed through damaged or burned skin. Following ingestion of large amounts of iron, peak serum levels generally occur within 2 to 6 hours. After ingestion, iron in the +2 state is oxidized to the +3 state and attached to the transport protein, ferritin. The iron is then released from the ferritin to transferrin in the plasma, transported to the blood forming storage sites, and incorporated into enzymes in the body. Iron is eliminated slowly from the body. Even in states of iron overload, children may lose up to 2 mg per day. Ingestion of less than 20 mg/kg elemental iron is likely to produce GI symptoms. For patients who ingest greater than 60 mg/kg elemental iron, potentially life threatening symptoms may occur.

Furthermore, the emergence of drug resistant parasites, e.g., malaria, has intensified the search for new therapeutic approaches (e.g. drug combinations). One new approach under investigation is the administration of iron chelating agents (Cabantchik, Z. I. et al. (1996) Acta Haematol. 95:70-77; Van Zyl, R. L. et al. (1992) J. Antimicrob. Chemother. 30:273-278).

Patients with transfusion iron-overload, iron poisoning, and drug resistant parasitic diseases (e.g., malaria) are commonly treated with low molecular weight iron chelators. These compounds remove the excess, toxic iron from the patient's blood. The most commonly used drug worldwide is desferrioxamine (Desferal®, Novartis). Therapy with desferrioxamine is effective, but under-utilized because of drug delivery problems. Oral absorption of desferrioxamine is very low. In some cases, desferrioxamine infusion has proven not to be adequate (Westlin, W. (1996) Clin. Ped. 5:531-535; Tenenbein, M. et al. (1992) Lancet 339:699-701; Adamson, I. Y. et al. (1993) Toxicol. Appl. Pharmacol. 120:13-19). In addition, the low molecular weight of this hydrophilic molecule (657 Da) leads to renal clearance in about 15 to 20 minutes. Consequently, the drug is given by continuous infusion over 12 to 16 hours. This is done either by subcutaneous infusion or by infusion into a permanent catheter. Such a long infusion duration is inconvenient and prone to infections and thrombosis. Desferrioxamine also has severe drawbacks in the treatment of parasitic diseases; (1) it is hydrophilic and poorly absorbed after oral administration; and (2) it is cleared rapidly after intravenous administration and iron chelators like desferrioxamine do not readily penetrate into advanced growth stages of parasitized cells (Loyevsky, M. et al. (1993)

J. Clin. Invest. 91:218-224). As a consequence, continuous infusion of iron chelators like desferrioxamine over a three day period is required to obtain enhanced parasite clearance in human malaria (Mabeza, G. F. et al. (1996) Acta Haematol. 95:78-86). Nonetheless, many patients use desferrioxamine suboptimally or not at all.

No other chelator has proven clinical efficacy. Searches for clinically effective alternatives to desferrioxamine for transfusional iron-overload have thus far been futile. Some chelating agents, such as diethyltriamine pentaacetic acid (DPTA) are effective, but too toxic for clinical use. Other chelators (e.g., EDTA) bind other cations in addition to iron, making them unacceptable as treatment of transfusional iron-overload or iron poisoning.

One approach to the problem has been to immobilize desferrioxamine to a large molecular matrix, thereby extending its biological half life. Immobilized desferrioxamine depends on a shift in "pseudoequilibrium" conditions to produce a net outflux of iron from cells. The vast amount of storage iron exists inside cells, however, effectively out of the reach of immobilized desferrioxamine. The problem is that the storage iron inside the cells remains a dangerous source of free radicals until it is chelated and inactivated by the Desferrioxamine in the matrix.

U.S. Pat. No. 5,534,241 ('241 patent) discloses chelation of iron using a linked molecule having a polymeric moiety covalently bonded to a lipid soluble anchor and a plurality of chelating agents covalently bonded to the polymeric moiety. There are several drawbacks to the compound disclosed in the '241 patent. In particular, complicated chemical synthesis and purification are required to covalently link the various groups. Also, to prevent rapid degradation of the '241 patent compound, surface protection is required. In addition, the polychelating agent is not free but is instead bound to the polymeric moiety, which can limit its ability to chelate iron from cellular stores.

The only chelator currently in extensive clinical trial is deferiprone (L1). Deferiprone removes excess iron reasonably well although it falls short of desferrioxamine in this regard (Collins, A. et al. (1994) Blood 83:2329-33). The great appeal of deferiprone over desferrioxamine is its oral absorption. For many patients, the convenience of an orally active chelator might more than compensate for lesser efficacy.

A number of clinical problems cloud deferiprone's future. Severe agranulocytosis occurs in about 2% of patients (al-Refaie, F. et al. (1992) Blood 80:593-9). Other significant side-effects of deferiprone include arthralgias and severe nausea (al-Refaie, F. et al. (1995) Br. J. Haematol. 91:224-229). Because of these and other problems, deferiprone's clinical future is far from assured. Therefore, there exists a need for an improved iron chelator delivery system to remove iron-overload in a cell, tissue, or organ.

SUMMARY

In accordance with a first aspect, a targeted iron chelator delivery system for treating iron-overload in mammalian tissues is provided. The delivery system includes free iron chelator, a targeting agent and a lipid carrier. In certain examples, the iron chelator is "free" in that it is not covalently bound to either the targeting agent or the lipid carrier, and, thus may dissociate from the lipid carrier and chelate excess iron in the target tissue. In certain examples, the targeting agent and/or the lipid carrier includes one or more cationic or anionic groups.

In accordance with another aspect, a targeted iron chelator delivery system for treating iron overload in the heart is disclosed. The delivery system includes an iron chelator and a lipid carrier. In certain examples, the lipid carrier includes an antibody that may bind to one or more cardiac proteins.

In accordance with an additional aspect, a targeted iron chelator delivery system for treating iron overload in the liver is provided. The delivery system comprises an iron chelator and a lipid carrier. The lipid carrier comprises a liver cell targeting agent for targeting at least one liver cell receptor. In certain examples, the liver cell targeting agent may be free in that it is not covalently bound to the iron chelator or the lipid carrier, but may be incorporated into the lipid carrier.

In accordance with yet another aspect, a targeted iron chelator delivery system is disclosed. The targeted iron chelator delivery system includes an iron chelator, a targeting agent, and one or more vesicles. The targeted iron chelator delivery system is designed for use in a method of treating iron-overload in a mammal by administering the delivery system to the mammal so that treatment occurs. In certain examples, the concentration of the iron chelator is about 1 µM to about 100 mM. In certain examples, the cross-sectional diameter of the vesicle(s) is about 10 nm to about 10 µm. In certain other examples, the vesicle(s) may be dissolved in a pharmaceutically acceptable excipient prior to administration, and the vesicle may be administered for a suitable period, e.g. about 20-30 minutes to about 3 hours. It will be recognized by the person of ordinary skill in the art, given the benefit of this disclosure, that the administration rate may vary depending on the composition of the liposome, the nature and identity of the selected iron chelator or other species to be included in the liposome, etc.

In accordance with a method aspect, a method of preparing a targeted iron chelator delivery system is disclosed. The method includes combining a lipid carrier, an iron chelator and a targeting agent selected for targeting the heart or liver to form targeted iron chelator-encapsulated vesicles, and extracting the targeted iron chelator-encapsulated vesicles to form a targeted iron chelator delivery system.

In accordance with another method aspect, a method of preparing a targeted iron chelator delivery system is provided. The method comprises dissolving one or more phospholipids in a suitable solvent, or mixture of solvents, to form a solution comprising an aqueous phase and an organic phase. An iron chelator and a targeting agent may then be added to the solution. The solution may then be vortexed to mix the aqueous and organic phases. The organic phase may then be removed by one or more suitable techniques, such as extraction, evaporation, etc. to form iron chelator encapsulated vesicles. The vesicles may be extruded through membrane filters, and non-encapsulated iron chelator may be removed using suitable separation techniques, e.g. centrifugation. The iron chelator-encapsulated vesicles may be removed or extracted to provide a targeted iron chelator delivery system.

In accordance with yet another method aspect, a method of preparing a targeted iron chelator delivery system is disclosed. The method includes drying a mixture of one or more phospholipids in a suitable solvent, or mixture of solvents, to form vesicles. The vesicles may then be hydrated by adding a solution including iron chelator. The resulting mixture may be vortexed to form iron chelator-encapsulated vesicles. The vesicles may be extruded through a membrane filter, and then dialyzed to purify the iron chelator-encapsulated vesicles. The purified iron-chelator encapsulated vesicles provide a targeted iron chelator delivery system.

In accordance with an additional method aspect, a method for treatment of iron overload is provided. In certain examples, the iron overload results from one or more blood transfusions. The method comprises administering to a mammal in need of treatment of iron overload from a blood transfusion a therapeutic amount of the targeted iron chelator delivery system. The targeted iron chelator delivery system may be any of the exemplary targeted iron chelator delivery systems discussed herein, and other targeted iron chelator delivery systems that will be recognized by the person of ordinary skill in the art, given the benefit of this disclosure. In certain examples, the targeted iron chelator delivery system may be dissolved in a suitable pharmaceutically acceptable carrier prior to administration to a mammal. In certain other examples, the targeted iron chelator delivery system may be administered prior to a blood transfusion, co-administered during a blood transfusion or administered after a blood transfusion. In other examples, the targeted iron chelator delivery system may be co-administered with one or more additional iron chelators, e.g. deferiprone.

In accordance with another method aspect, a method of preventing iron overload from a blood transfusion is disclosed. The method includes administering to a mammal receiving a blood transfusion an iron chelator delivery system. In certain examples, the iron chelator delivery system is co-administered with the blood transfusion.

The novel targeted iron chelator delivery systems disclosed here, and methods for their use, provide robust systems for removal of excess iron that may result from iron overload due to blood transfusion or that may result from one or more medical or genetic disorders. These and other illustrative aspects, examples and embodiments are discussed in detail below.

BRIEF DESCRIPTION OF THE DRAWINGS

Certain illustrative examples are described below with reference to the accompanying drawings in which:

FIG. 3 is a table that shows iron content and hepatic index, in accordance with certain examples;

FIG. 7A is a graph showing measurements of left ventricle systolic pressure (LVP) and left ventricle end-diastolic pressure (closed bars of FIG. 7A), in accordance with certain examples;

FIG. 7B is a graph showing measurements of LV +dP/dt (open bars of FIG. 7B), and −dP/dt (closed bars of FIG. 7B), in accordance with certain examples;

FIG. 7C is a graph showing the measurement of the time constant of relaxation (tau) in adult rat hearts from Sprague Dawley iron overloaded and non-iron overloaded rats, in accordance with certain examples;

FIG. 13 is a table of blood chemistry values before and after liposome infusion (with and without desferrioxamine), in accordance with certain examples;

FIGS. 29A and 29B are fluorescence micrographs showing mannosylated liposome distribution in the heart and liver, in accordance with certain examples;

FIGS. 30A and 30B are fluorescence micrographs showing cationic liposome distribution in the heart and liver, in accordance with certain examples;

Figure 1:
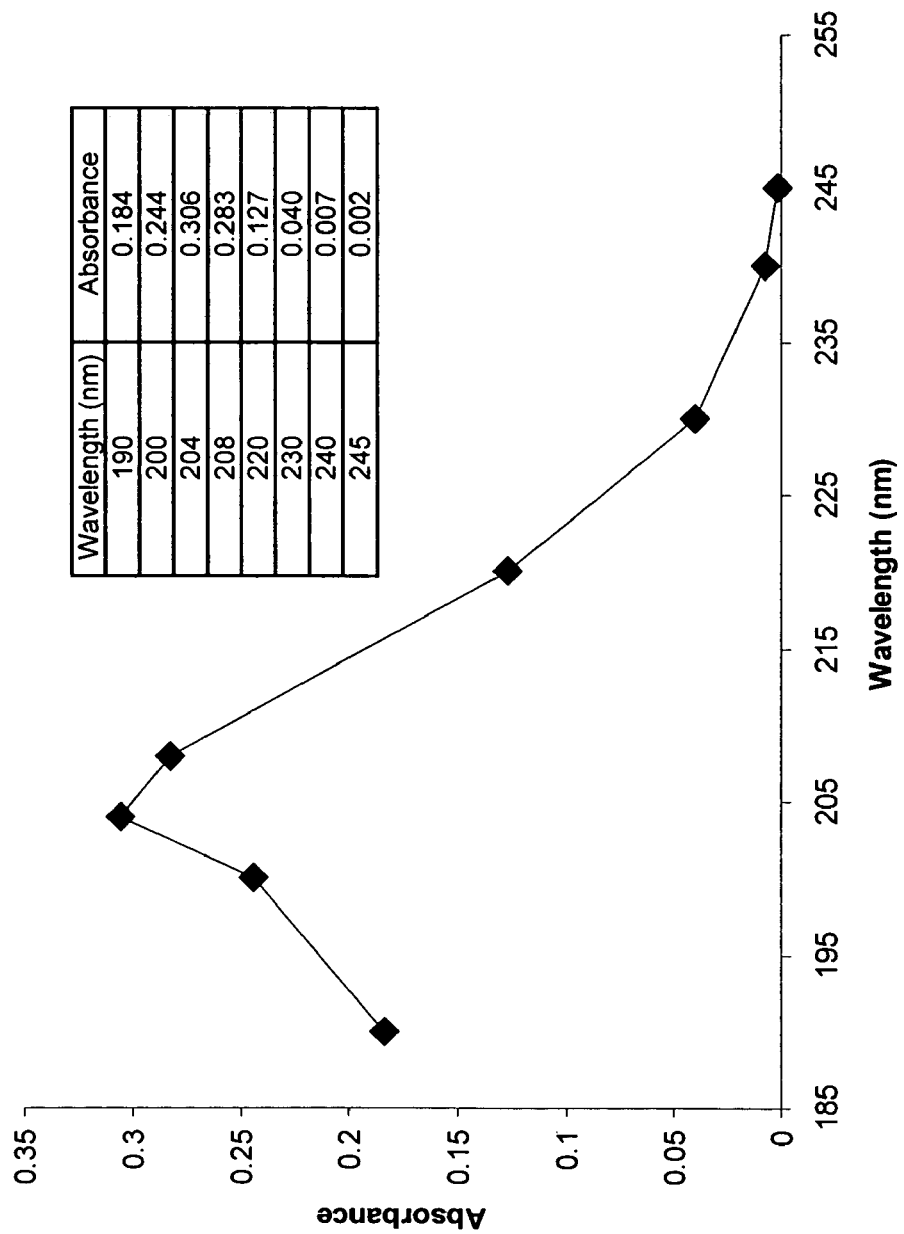
FIG. 1 is an absorbance spectrum and corresponding data for desferrioxamine (DFO), in accordance with certain examples.

It will be recognized by the person of ordinary skill in the art, given the benefit of this disclosure, that the exemplary figures described herein are presented to facilitate a better understanding of the illustrative aspects, examples and embodiments provided in this disclosure, and, as such, the figures should not be construed as limiting the full scope of the targeted iron chelator delivery system disclosed here.

DETAILED DESCRIPTION OF CERTAIN EXAMPLES

It will be recognized by the person of ordinary skill in the art, given the benefit of this disclosure, that examples of the targeted iron chelator delivery system disclosed here represent a significant technological advance. Efficacious targeted iron chelator delivery systems may be designed to provide rapid iron removal in a specific cell, tissue, organ or organs with minimal toxicity and minimal side-effects. The target iron chelator delivery system disclosed here provides numerous advantages over existing therapies designed to remove excess iron. For example, the kidneys rapidly excrete small, hydrophilic iron chelator molecules, such as desferrioxamine. Without wishing to be bound by any particular scientific theory, examples of the iron chelator delivery system disclosed here, e.g., iron chelators associated with lipid carriers, liposomes, and one or more targeting agents, may be designed to be too large to be filtered by the renal glomeruli. For example, small liposomes that are about 10 nm in diameter are of sufficient size to be above the filtration limit of the glomeruli of the kidneys. The biological half-life of the iron chelator may be extended using the targeted iron chelator delivery system disclosed here and certain specific cells, tissues or organs may be targeted to reduce the amount of iron present in the targeted cells, tissues or organs.

The more user-friendly terms "include" and "includes," as used throughout this disclosure, should be understood to be interchangeable with the open ended terms "comprises" and "comprising."

Conventional iron chelation therapy, e.g. desferrioxamine therapy, may cost between about $12,000 and $15,000 per year. Much of the expense involves the portable home infusion pumps, associated equipment (e.g., sterile infusion tubing and needles), and home nursing visits. These costs may be reduced by using the targeted iron chelator delivery system disclosed here. In addition, examples of the targeted iron chelator delivery system provided here may be made available to underdeveloped countries that lack the financial resources needed for conventional iron chelation therapies. Also, the targeted iron chelator delivery system disclosed here reduces and/or eliminates the problems of local reactions associated with the subcutaneous administration of some iron chelators. For example, the chelator diethyltriamine pentaacetic acid (DTPA) has been used to treat iron-overload, but this compound can cause severe local reactions that has led to discontinuation of its use. Intravenous administration, although more efficacious, is associated with the risk of infection, atrial thrombosis, and subclavical thrombosis. In addition, an indwelling catheter may curl into the atrium causing cardiac irritation and thrombosis, and right atrial thrombosis can lead to life threatening pulmonary embolism. Examples of the targeted iron chelator delivery system disclosed here may overcome or avoid these and other problems associated with iron chelation therapy. In at least certain examples, the targeted iron chelator delivery system provided here delivers iron chelator more efficiently than conventional methods. Lower amounts of iron chelator may be used and combined with lipid carriers, e.g., vesicles, to deliver the iron chelator to a specific cell, tissue or organ to increase the local concentration of the iron chelator. Other advantages of certain examples of the targeted iron chelator delivery system include, but are not limited to, reduced toxicity based on the administration of a lower dose for a shorter period of time, targeted delivery of the iron chelator without high renal clearance, an increase in the half life of the iron chelator via targeted delivery of the drug to the heart and the liver, thus, reducing the amount of drug needed, and entrapment of the drug in the liver up to 5 days, thus, allowing a longer period of time for iron chelation. Some iron chelator from the liver parenchyma can also redistribute to other tissues and bind free iron.

In accordance with certain examples, a targeted iron chelator delivery system for treating iron-overload in mammalian tissues is provided. In certain examples, the targeted iron chelator delivery system comprises an iron chelator, a targeting agent, and a lipid carrier. As used here "targeted" refers to specificity or selectivity of the iron chelator delivery system for a specific cell type, tissue or organ. For example, in iron chelator delivery systems targeted at reducing iron-overload in the heart, the system may include a recognition site, e.g., a site or binding portion of an enzyme, protein, antibody, etc., for one or more cardiac markers, such as polysaccharides, lipids, proteins, etc. In iron chelator delivery systems targeted at reducing iron-overload in the liver, the system may include one or more recognition sites for a liver receptor or marker, e.g., a protein, polysaccharide, lipid, etc. located primarily in the liver. Similarly, the iron chelator delivery system may be configured to target any specific tissue or organ by including a molecule or group that may recognize or bind to a marker on the target tissue or organ. Suitable markers include, for example, those markers discussed above, e.g. proteins, lipids, polysaccharides, etc., and other markers that will be recognized by the person of ordinary skill in the art, given the benefit of this disclosure.

In accordance with certain examples, the iron chelator of the targeted iron-chelator delivery system is selected for its ability to remove iron, e.g. free iron and/or bound iron, in one or more specific tissues or organs. The term "iron chelator" refers to a compound that can remove excess iron from the patient's blood, tissues and/or organs. In certain examples, the iron chelator may be selected such that it binds tightly to iron. In other examples, the iron chelator is selected so that it binds to iron with a lower binding constant than normal hemoglobin. In certain examples, two or more iron chelators are used to provide enhanced removal of iron from a specific cell-type, tissue or organ. For example, a first iron chelator may be selected that has a high iron-binding constant but has low bioavailability, and a second iron chelator may be selected that has high bioavailability but binds iron with a lower binding constant than the first iron chelator. Other examples of combining two or more iron chelators will be recognized by the person of ordinary skill in the art, given the benefit of this disclosure. Exemplary iron chelators for use in the targeted iron delivery system disclosed here, include but are not limited to, hydrophilic molecules having charged groups that may bind to or associate with iron. In certain examples, the iron chelator includes one or more amino or carboxy groups that can bind to iron. Depending on the pH and on the nature of the group, the charged groups may be positively charged or negatively charged. Exemplary iron chelators include, but are not limited to, desferrioxamine, deferiprone, PIH (pyridoxal isonicotinoyl hydrazone), rhodotorulic acid, HBED (N,N'-Bis(2-hydroxybenzyl)ethyl-enediamine-N,N-diacetic acid), HBPD (N,N'-Bis(2-hydroxybenzyl)propylene-1,3-diamine-N,N-diacetic acid), 2,3-dihydroxybenzoic acid, DTPA (diethyltriamine pentaacetic acid), and iron chelators produced by bacterial siderophores. The concentration of the iron chelator may vary depending on numerous factors including, for example, the binding constant of the iron/iron chelator complex, bioavailability, clearance rate, etc. In certain examples the iron chelator is present in a concentration from about 1 nM to about 500 mM, more particularly from about 500 nM to about 250 mM, e.g. about 1 μM to about 100 mM. In other examples, the iron chelator is present in an effective or therapeutic amount. As used here "therapeutic amount" refers to an amount sufficient to reduce, alleviate or ameliorate pathological symptoms associated with a disease or disorder. It should be understood that a therapeutic amount does not necessarily remove all excess iron, but instead removes sufficient amounts of iron such that the symptoms are reduced, alleviated or ameliorated. It will be within the ability of the person of ordinary skill in the art, given the benefit of this disclosure, to select suitable concentrations of iron chelator for use in the targeted iron chelator delivery system disclosed here.

In accordance with other examples, the lipid carrier of the targeted iron chelator delivery system may take numerous forms including, for example, micelles, vesicles, liposomes, etc. In certain examples, the amount of lipid used is above the critical micelle concentration such that micelles or vesicles are the predominant form in solution. In some examples, lipid bilayers associate to form unilamellar vesicles, paucilamellar vesicles or multilamellar vesicles, e.g. small unilamellar vesicles (SUVs), large unilamellar vesicles (LUVs), giant unilamellar vesicles (GUVs), targeted chelate nanoparticles, polymeric carriers, etc. The term "liposome" is used in the broad sense and should be understood to include unilamellar vesicles, paucilamellar vesicles, multilamellar vesicles and other forms and configurations that vesicles can take. In certain examples, the lipid carrier may be formed and the iron chelator can be disposed within a cavity of the lipid carrier, e.g. is encapsulated within the lipid carrier. In other examples, the iron chelator may be intercalated in a membrane of the lipid carrier or associated with the outer surface of the lipid carrier. For example, a hydrophilic iron chelator, such as desferrioxamine, may be combined with a lipid carrier. In yet other examples, the iron chelator may be coated with the lipids of the lipid carrier, e.g., iron chelators associated, intercalated, or attached to the surface of lipid molecules or to the lamellae of a lipid carrier. Other examples of lipid carrier formulations for the present iron chelator delivery system include, for example, the following: systems used with amphotericin B, which involve complexing the active ingredient with phospholipids as used in the formulation for ABELCET® (The Liposome Company, Inc., Princeton N.J.); cholesteryl sulfate complexes for injection similar to the formulation used for AMPHOTEC® (Sequs Pharmaceuticals, Menlo Park, Calif.) which comprises a sterile, pyrogen-free, lyophilized powder for reconstitution and intravenous administration, e.g., a formulation comprising a complex of desferrioxamine and cholesteryl sulfate (upon reconstitution a colloidal dispersion of microscopic disc-shaped particles result); and a single bilayer liposomal drug delivery system such as used with AmBisome® (Nexstar Pharmaceuticals, Boulder Colo. (taken over by Gilead Sciences Foster City, Calif.)), wherein single bilayer liposomes are used. In certain examples, the drug becomes active when the lipid carrier, e.g., the liposome, fuses with cells to release its content. In some examples, chelates may be attached to targeted carriers by bonds that are broken when the carriers are internalized into iron overloaded cells. Without wishing to be bound by any particular scientific theory, the iron chelator can interact with the liposome structure through numerous forces, e.g. hydrophobic interactions, hydrogen bonding, van der Waals interactions, and the like, such that the iron chelator is associated with the liposome for a sufficient time to allow for delivery of the iron chelator delivery system to a specific target cell, tissue, organ or system.

In accordance with other examples, the lipid carrier of the targeted iron chelator delivery system may comprise numerous different lipids, e.g., polar, non-polar, charged, uncharged, amphipathic lipids, or may comprise substantially a single type of lipid or a single lipid. Exemplary lipids for use in the lipid carrier disclosed here include phospholipids, glycerophospholipids, ether glycerophospholipids, sphingolipids, waxes and suitable molecules having a polar head group and a non-polar tail. Exemplary phospholipids include, but are not limited to, phosphatidylcholine, phosphatidylethanolamine, phosphatidylserine, phosphatidylglycerol, diphosphatidylglycerol, and phosphatidylinositol. The lipid carrier may further include additional compounds, such as, for example, terpenes, steroids, and the like that can change the properties of the lipid carrier, e.g. can alter the membrane fluidity of the lipid carrier. In certain examples, the lipid carrier includes cholesterol within the membrane. The lipid carriers used in the targeted iron chelator delivery system disclosed here have a number of advantages over currently used options, such as red cell ghosts, as encapsulation agents. For example, vesicles may be manufactured, while red cells ghosts are harvested. Use of red cell ghosts also entails some exposure, even slight, to biological pathogens. Finally, lipid carriers, e.g., liposomes, avoid alloimmunization issues because they lack red cell antigens (Rose, W. et al. (1990) Blood 76:1431-7).

In accordance with certain other examples, the targeting agent of the targeted iron chelator delivery system is selected for its ability to recognize a specific marker. The targeting agent may take numerous forms depending on the type of marker selected and depending on the dosage requirements, bioavailability, clearance rate, etc. The targeting agent typically is a protein that can recognize one or more sites on the target cell, tissue or organ to deliver the lipid carrier containing the iron chelator to that cell, tissue or organ or within suitable proximity to allow the iron chelator to bind to excess iron. Suitable targeting agents will be selected by the person of ordinary skill in the art, given the benefit of this disclosure. Exemplary targeting agents include enzymes, antibodies, e.g. monoclonal and polyclonal antibodies, and other biomolecules that can bind to a protein, polysaccharide, lipid, etc. with high specificity. Such targeting agents may be reconstituted in the lipid carrier using numerous methods including, for example, those methods described in U.S. Pat. No. 4,483, 929, the entire disclosure of which is incorporated herein by reference for all purposes. Other suitable methods for incorporating targeting agents will be recognized by the person of ordinary skill in the art, given the benefit of this disclosure.

In certain examples, the targeting agent is an antibody that is designed to bind to one or more cardiac markers, e.g., one or more up-regulated modulatory proteins present in pathogenic cardiocytes. Cardiac failure as a result of iron-overload is of great clinical importance. The heart can be targeted for delivery of suitable amounts of the iron chelator delivery system, disclosed here. In certain examples, desferrioxamine may be combined with a lipid carrier by placing a positive or negative charge on the lipid carrier and/or by attaching antibodies specific to cardiac, vascular, endothelial, and matrix proteins to the lipid carrier. For example, the targeting agent may be designed to target myosin, troponin, or myosin light chain proteins, vasculature proteins, endothelial cells, or matrix proteins. The lipid carrier may also be tagged with cardiac imaging labels. In addition, selected delivery routes and an increase in the half life of the lipid carrier can enhance delivery to the heart.

In certain other examples, the targeting agent is designed to target one or more liver markers. For example, the targeting agent can be designed to target one or more liver receptors that bind to asialoglycoprotein, galactose and mannose. In addition and without wishing to be bound by any particular scientific theory, most of the lipid carrier molecules are trapped by the liver and engulfed by the Kupfer cells and hepatocytes in the liver. The targeted iron-chelator delivery system disclosed here takes advantage of this seemingly unfavorable side-effect. Reticuloendothelial (RE) cells can engulf the iron chelator delivery system, which places the iron chelator in a position to intercept iron as it is released from erythrocytes degraded by the liver. Other suitable cardiac and liver markers for targeting will be selected by the person of ordinary skill in the art, given the benefit of this disclosure.

In accordance with certain other examples, one or more tags may be added to the lipid carrier. The tags can provide information about the local environment of the delivery system, e.g. whether or not the delivery system has been taken-up by a cell, tissue or organ. Suitable tags include but are not limited to fluorescent tags, such as fluorescein isothiocyanate (FITC), didansyl chloride, and other suitable probes that can be reacted with the lipid carrier or the targeting agent of the targeted iron chelator delivery system disclosed here. In certain examples, one or more magnetically active tags such as nitroxide spin labels, magnetically active nuclei, etc. may be used. In other examples, one or more radioactive tags, such as $^{35}$S, $^{32}$P, $^{99}$Tm, $^{111}$In, etc. can be added to the iron chelator delivery system. In certain other examples, one or more colorimetric labels, e.g. colored dyes, enzymes that can react with a substrate to produce a colored product, etc., may be added to the iron chelator delivery system. Other suitable tags will be readily selected by the person of ordinary skill in the art, given the benefit of this disclosure.

In accordance with certain other examples, a targeted iron chelator delivery system for treating iron overload in the heart is disclosed. The targeted iron chelator delivery system includes an iron chelator, such as, for example, any one or more of the iron chelators discussed herein. In certain examples, the iron chelator typically is selected from one or more of the following: desferrioxamine, deferiprone, PIH, rhodotorulic acid, HBED, HBPD, 2,3-dihydroxybenzoic acid, DTPA, and iron chelators produced by bacterial siderophores. In certain examples, the iron chelator is present in a therapeutic amount. In other examples, the concentration of iron chelator is about 1 μM to about 100 mM, more particularly from about 100 μM to about 10 mM, e.g. from about 1 mM to about 5 mM. The delivery system further includes a lipid carrier, such as those discussed herein. In certain examples, the lipid carrier comprises an antibody for targeting at least one cardiac protein, e.g. cardiac myocyte proteins, vasculature proteins, endothelial cells, matrix proteins, myosin, troponin, and myosin light chain. In certain other examples, the lipid carrier is a liposome. In examples where the lipid carrier is a liposome, the lipid carrier may have a cross-sectional diameter of about 10 nm to about 10 μm. In examples using liposomes, the iron chelator may be encapsulated within the central cavity of the liposome, intercalated into the liposome bilayer, or associated with the outer surface of a membrane of the liposome. In examples using multilamellar liposomes, the iron chelator may be encapsulated between lamellae of the liposomes, intercalated into one or more of the bilayers of the multilamellar liposomes, or associated with the outer surface of the multilamellar liposomes.

In accordance with certain other examples, a targeted iron chelator delivery system for targeting the heart is disclosed. The targeted iron chelator delivery system includes an iron chelator and a carrier, such as, for example, a lipid carrier. The lipid carrier includes a targeting agent for targeting the heart. The targeting agent and/or lipid carrier may include one or more cationic and/or anionic groups. In certain examples, the cationic or anionic groups are carboxy groups, amino groups, hydroxy groups and other suitable positively and/or negatively charged groups.

In accordance with certain other examples, a targeted iron chelator delivery system for treating iron overload in the liver is provided. The delivery system includes an iron chelator, and a lipid carrier. The lipid carrier includes a liver cell targeting agent for targeting at least one liver cell receptor or liver cell protein. Exemplary liver receptors and proteins include, but are not limited to, receptors that bind to asialoglycoprotein (e.g. hepatocyte asialoglycoprotein receptor), galactose, and mannose (e.g. a Kupffer cell mannose receptor), and receptors on liver endothelial cells. The iron chelator may be selected from any of those iron chelators discussed herein, e.g. desferrioxamine, deferiprone, PIH, rhodotorulic acid, HBED, HBPD, 2,3-dihydroxybenzoic acid, DTPA, and iron chelators produced by bacterial siderophores, and other suitable iron chelators selected by the person of ordinary skill in the art, given the benefit of this disclosure. The concentration of the iron chelator can vary, for example, from about 1 μM to about 100 mM. In certain examples, the iron chelator is present in a therapeutic amount. The lipid carrier may take the form of liposomes, multilamellar vesicles and other ordered structures that may be formed with lipids and/or phospholipids.

In accordance with certain examples, a method of preparing a targeted iron chelator delivery system is disclosed. The method includes combining a lipid carrier, an iron chelator and a targeting agent selected for targeting the heart or liver to form targeted iron chelator-encapsulated vesicles. The targeted iron-chelator encapsulated vesicles may then be extracted or removed to provide a targeted iron chelator delivery system. The iron chelator, lipid carrier and targeting agent each may be selected from any of the iron chelators, lipid carriers and targeting agents discussed herein and other suitable iron chelators, lipids carriers and targeting agents that will be selected by the person of ordinary skill in the art, given the benefit of this disclosure.

In accordance with certain other examples, a method of preparing a targeted iron chelator delivery system is provided. The method includes dissolving suitable phospholipids, e.g. phosphatidylcholine and optionally a steroid, e.g. cholesterol, in a suitable solvent, e.g. dichloromethane, ether, chloroform, methanol, etc., or solvent mixture, to form a solution comprising an aqueous phase and an organic phase. To this solution is added an iron chelator and a targeting agent. The solution with added iron chelator and targeting agent is vortexed to mix the aqueous and organic phases. The solution is then subjected to an extraction step and/or an evaporative step to remove the organic phase. Such extraction or evaporative step may be performed under vacuum, e.g. using a rotovap or similar device, to form iron chelator-encapsulated vesicles, e.g. iron chelator encapsulated liposomes. The vesicles may then be extruded through suitable membrane filters. Non-encapsulated iron chelator may then be removed by filtration, centrifugation or other suitable separation techniques. The iron chelator encapsulated-liposomes may then be removed to provide a targeted iron chelator delivery system, which can be stored until use.

In accordance with yet other examples, a method of preparing a targeted iron chelator delivery system is disclosed. The method includes drying a mixture of a lipid carrier, e.g. phosphatidylcholine and optionally a steroid, e.g. cholesterol, in a suitable solvent, e.g. dichloromethane, ether, chloroform, methanol, etc., or mixture of solvents, to form vesicles. The mixture may be dried under vacuum, under nitrogen, under argon, or under inert environments. The dried mixture can be hydrated by adding an aqueous solution of iron chelator followed by vortexing to form iron chelator-encapsulated vesicles. The iron-chelator encapsulated vesicles may be extruded through membrane filters. The vesicles may be centrifuged or dialyzed to purify the iron chelator-encapsulated vesicles.

In accordance with certain other examples, the targeted iron-chelator delivery system disclosed here can be pre-administered, co-administered, or post-administered to subjects receiving transfusion. For example, mammals, e.g., humans or animals, often receive blood on a three to six week schedule, depending on the severity of their anemia. The targeted iron chelator delivery system disclosed here may be used to prevent or reduce transfusional iron-overload. For example, desferrioxamine may be combined with a lipid carrier, e.g., a liposome, and the resulting product can be administered pre-transfusion, during transfusion, or at the end of a transfusion session. The targeted iron chelator delivery system can be administered continuously, intermittently, periodically, etc., and may be administered using suitable routes, such as oral administration, rectal administration, subcutaneous administration, iv or arterial infusion or injection, administered in a suppository, nasally, and other suitable methods for administration that will be selected by the person of ordinary skill in the art, given the benefit of this disclosure. Such treatment using the targeted iron chelator system disclosed here would allow significant improvement over the current daily use of an infusion pump for 12-16 hours intervals. For example, thirty grams of desferrioxamine encapsulated by vesicles may be sufficient to supply enough chelator for a month. This approach would be simpler than any available to date, including oral administration of deferiprone. The person of ordinary skill in the art will recognize, given the benefit of this disclosure, that the exact dosage and dose schedule may vary depending on the subject's characteristics, e.g. age, weight, health, human mammal, non-human mammal, etc. In some examples, the targeted iron chelator delivery system may be mixed or added to the blood transfused into the mammal, e.g. the blood and iron chelator delivery system are mixed and then the combination is transfused into a human or non-human mammal. It is a significant advantage that examples of the targeted iron chelator delivery system disclosed here can be administered prophylactically to prevent iron overload in individuals prior to, or during, blood transfusion.

In accordance with certain examples, the targeted iron chelator delivery system may be dissolved in a pharmaceutically acceptable carrier prior to administration. As used herein "pharmaceutically acceptable carrier" includes any and all excipients, solvents, dispersion media, coatings, antibacterial and antifungal agents, toxicity agents, buffering agents, absorption delaying or enhancing agents, surfactants, and micelle forming agents, lipids, liposomes, and liquid complex forming agents, stabilizing agents, and the like. Suitable media and agents for pharmaceutically active substances will be readily selected by the person of ordinary skill in the art, given the benefit of this disclosure. Supplementary active compounds may also be incorporated into the compositions.

In accordance with additional examples, a targeted iron chelator delivery system is provided. The targeted iron chelator delivery system includes an iron chelator, a targeting agent, and one or more vesicles. The targeted ion chelator delivery system is configured for use in a method of treating or preventing iron-overload in a mammal. The delivery system is administered to the mammal so that treatment occurs, e.g. so that a suitable amount of excess iron is removed from the target cell, tissue or organ. In certain examples, the concentration of the iron chelator is about 1 μM to about 100 mM, and the size of the vesicle is about 10 nm to about 10 μm. The vesicle may be dissolved in a pharmaceutically acceptable excipient prior to administration, and can be administered for a suitable period, e.g. intravenous administration for about 20-30 minutes to about 3 hours at a rate of about 50 cc/hour in normal saline (0.9% NaCl).

In certain examples the iron chelator delivery system takes the form of a gel, a lozenge, a spray, a tablet, an oral suspension, etc. The delivery system may be administered locally by injection, by catheterization, etc., may be administered systemically by intravenous infusion or arterial infusion, may be administered topically, subcutaneously, may be administered rectally, may be administered by inhalation and through other suitable methods. In certain examples, the targeted iron chelator delivery system is delivered through a catheter that is inserted proximate to the target organ. For example, a catheter may be inserted into the hepatic artery to provide delivery of the iron chelator delivery system to the liver, may be inserted into the inferior vena cava or a coronary artery to provide delivery of the iron chelator delivery system to the heart, etc. The exact dosage may vary depending on the desired level of iron to be removed, the nature of the iron chelator, etc. In certain examples, the dosage is selected such that from about 1 to about 30 mg of iron chelator/kg of body weight is administered at each dose, more particularly about 5 to about 25 mg of iron chelator/kg of body weight is administered at each dose, e.g. about 10, 15 or 20 mg iron chelator/kg of body weight is administered at each dose. The iron chelator delivery system may be administered continuously, hourly, daily, weekly, monthly, semi-monthly, or other suitable schedule. In certain examples the delivery system may be administered in bolus or may be administered intermittently. In examples where the delivery system takes the form of a liquid, suspension or solution, the delivery system may be administered at a rate of about 50 cc/hour to about 250 cc/hour, more particularly from about 100 cc/hour to about 200 cc/hour, e.g., about 150 cc/hour.

In accordance with certain examples, the targeted iron chelator delivery system may take the form of a dried powder, e.g. a lyophilized powder, such that storage and transport of the delivery system is simplified. Prior to administration, the dried powder can be rehydrated in a suitable solvent or excipient and administered to a human or non-human mammal as prophylaxis to prevent iron overload or to treat iron overload in the human or the non-human mammal in need of such treatment.

In accordance with certain examples, methods and compositions comprising liposomes and antibiotics or antifungals are provided. For example, a commercially available liposome that carries an antifungal is AMBISOME® available from Fujisawa Healthcare, Inc. (Deerfield, Ill.). The antibiotic or antifungal liposomes can be administered alone or co-administered with one or more of the targeted iron chelator delivery systems disclosed herein, e.g., to prevent or treat secondary infection. The exact administration rate of antibiotic and antifungal containing liposomes may vary, and in certain examples, the liposomes are administered at a rate of about 50-250 cc/hour in normal saline (0.9% NaCl), more particularly about 150-250 cc/hour in normal saline, e.g., about 200-250 cc/hour in normal saline.

Certain specific examples are described below to illustrate the features and advantages of the targeted iron chelator delivery systems disclosed here. The contents of all references, patents and published patent applications cited throughout this application are hereby incorporated by reference in their entirety for all purposes.

Example 1

Preparation of an Iron Chelator Delivery System

Iron chelator delivery systems comprising an iron chelator and a lipid carrier, e.g., a liposome, may be prepared using the following standard procedures. General methods for preparing liposomes for use in the present iron chelator delivery systems are provided in Cortesi R., Esposito E., Gambarin S., Telloli P., Menegatti E., Nastruzzi C. (1999) "Preparation of liposomes by reverse-phase evaporation using alternative solvents," Journal of Microencapsulation 16(2):251-256; Buboltz J. T., Feigenson G. W., (1999) "A novel strategy for the preparation of liposomes: rapid solvent exchange," Biochimica et Biophysica Acta 1417(2):232-245; Bandyopadhyay P., Kren B. T., Ma X., Steer C. J., (1998) "Enhanced gene transfer into HuH-7 cells and primary rat hepatocytes using targeted liposomes and polyethylenimine," Biotechniques 25(2):282-284, 286-292; Puu G., Gustafson I., (1997) "Planar lipid bilayers on solid supports from liposomes-factors of importance for kinetics and stability," Biochimica et Biophysica Acta 1327 (2):149-161; Weiner A., (1994) "Liposomes for protein delivery: selecting manufacture and development processes," Immunomethods 4(3):201-209, the contents of which are incorporated herein by reference.

To determine the $\lambda_{max}$ value for Desferrioxamine, a solution of desferrioxamine mesylate in methanol is prepared and absorbance spectra determined using a Perkin Elmer Lambda 3B UV/VIS Spectrophotometer (FIG. 1).

Figure 2:
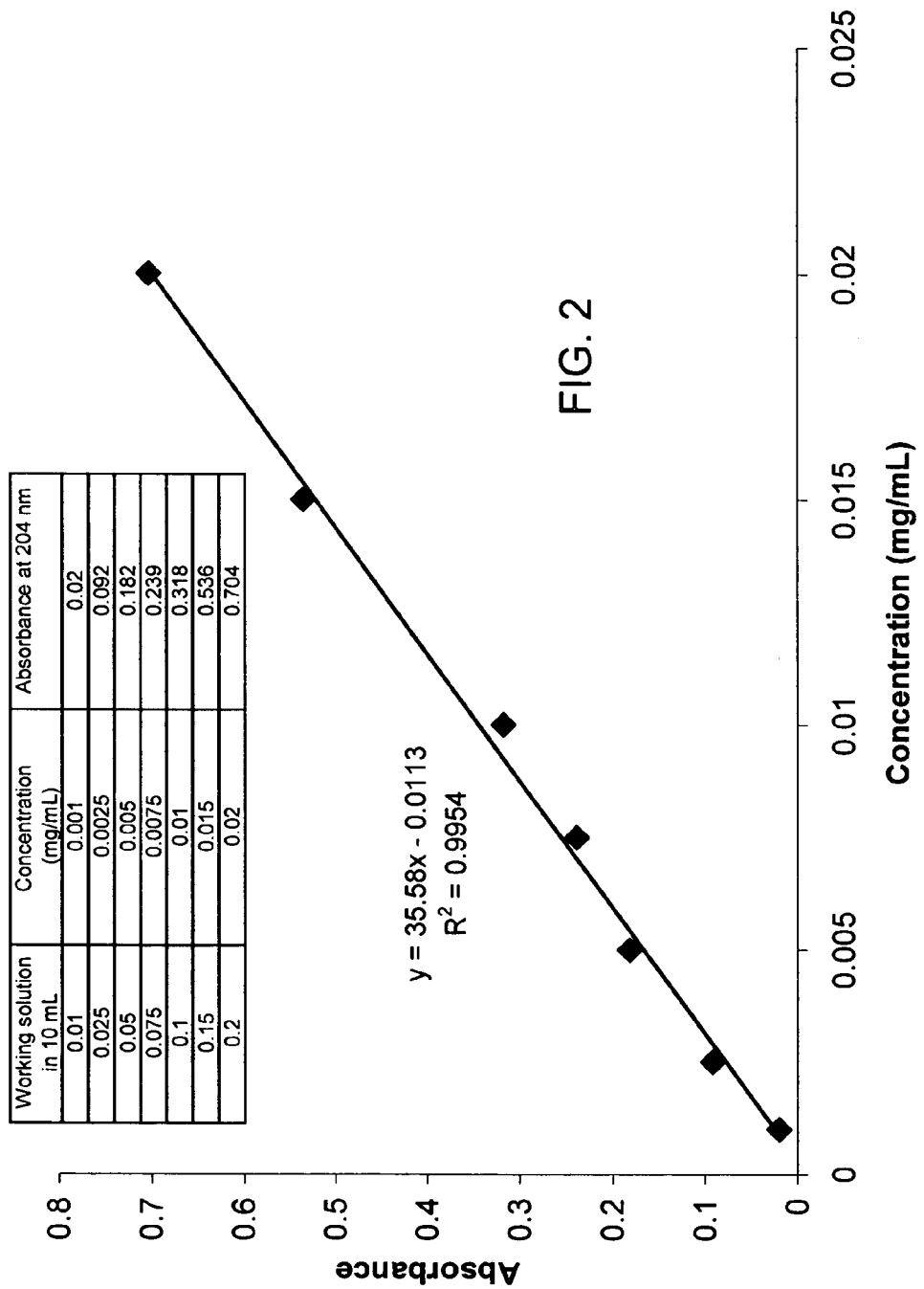
FIG. 2 is a calibration curve and corresponding data for DFO, in accordance with certain examples.

To obtain a calibration curve (FIG. 2), 10 mg desferrioxamine mesylate is dissolved in 1200 ml of methanol and a stock solution generated. 0.1 mL, 0.25 mL, 0.5 mL, 0.75 mL, 1.0 mL, 1.5 mL, and 2.0 mL of this stock solution is transferred to separate volumetric flasks to form a final volume of 10 mL with the addition of methanol. Spectrophotometric absorbance for each flask is read at 204 nm.

Method 1: Liposomes are prepared by the reverse phase evaporation technique (Tabak, A. et al. (1994) J. Pharm. Pharmacol. 46:789-796). Phosphatidylcholine (PC) 0.5 mg and 4.5 mg cholesterol (Ch) are dissolved in 4 mL of chloroform ($CHCl_3$). The aqueous phase containing 12 mg desferrioxamine mesylate in 2 mL of saline is added to the above organic phase. The two phases are vortexed for 4 minutes for formation without emulsion. Liposomes are obtained by evaporating the organic phase under a partial vacuum produced by a water aspirator on a rotary evaporator at 20° C.-30° C. The resulting liposomes are extruded through 1.0, 0.6, 0.4, and 0.2 µm polycarbonate filters from Nucleopore™ or Poretics Corp. Polycarbonate membrane filters sequentially (membrane filter pore sizes may be varied to obtain liposomes of larger sizes). The non-liposomal desferrioxamine is removed using a Sephadex™ G-25 (Sigma) spin-column and centrifugation. Briefly, the bottom of a 3 ml disposable syringe (0.5 cm internal diameter) is plugged with clean, silanized glass wool. A Sephadex™ G-50 (slurry is loaded into the syringe-column. The syringe is placed into a 15 ml polypropylene tube and spun for 3 minutes at 12,500 rpm in order to pack the column. A 0.25 mL sample is then loaded onto the column and centrifuged for 3 minutes at a speed of 1500 rpm. Twenty-five µL of eluant is transferred to a volumetric flask and made up to a final volume of 10 mL with methanol. The flask is then shaken to extract intraliposomal desferrioxamine. Spectrophotometric absorbance of the solution is determined at 204 nm.

Method 2: A mixture of phosphatidylcholine (PC) and cholesterol (16 mg PC: 8 mg Ch) in methanol is dried under a stream of nitrogen and vacuum desiccated for 2 hours to remove any remaining traces of the solvent. The lipid is then hydrated by addition of 14 mg of desferrioxamine in 4 mL of saline. Saline is passed through a Chelex column. The mixture is vortexed for 5 minutes. The resulting liposomes are extruded through 1.0, 0.6, 0.4, and 0.2 µM Nuclepore™ polycarbonate membrane filters, sequentially (membrane pore sizes may be varied to obtain liposomes of larger sizes). Liposomes are dialyzed overnight against saline at 4° C. to remove non-encapsulated desferrioxamine. Intraliposomal desferrioxamine is assayed by dissolving an aliquot of the suspension in an equal volume of Triton-X 100, adding $FeCl_3$ in 0.1 M HCl and measuring the absorbance of the iron-desferrioxamine complex at 428 nm (Young, S. P., et al. (1979) Brit. J. Haem. 41:357-363).

Example 2

Preparation of Radiolabeled Liposomes with [111]In

Desferrioxamine is prepared by activation of the carboxylic groups of desferrioxamine with carbodiimide at pH 4.0 using a method similar to that described by Khaw et al. (Khaw, B. A. et al. (1991) J. Nucl. Med. 32:1742-1751). In brief, $8.33 \times 10^{-5}$ mM desferrioxamine in 250 µL $H_2O$ (pH adjusted to 4.0) is mixed with 14-fold molar excess of N-hydroxy sulfosuccinimide (NHSS) and 400 µg/40 µL 1-ethyl-3-(3-dimethylamino-proply) carbodiimide (EDC) is added. Another aliquot of NHSS is added. The reaction is allowed to proceed for 5 minutes at room temperature. The activated desferrioxamine is added then directly into 1 mg of phosphatidylethanolamine (PE) in 0.1 M borate buffer at pH 8.3. At this pH, there is unidirectional coupling of the carboxyl group of the activated desferrioxamine to the amino group of the phosphatidylethanolamine. Free desferrioxamine is separated from desferrioxamine-PE by lyophilization of the mixture and separation of the desferrioxamine-PE by extraction with chloroform. Without wishing to be bound by any particular scientific theory, desferrioxamine will not be soluble, but desferrioxamine-PE will be soluble. The chloroform is evaporated to obtain desferrioxamine-PE. Aliquots of desferrioxamine-PE are solubilized in 0.5 M citrate pH 5.0 to which 1-2 mCi of $^{111}$In is added. The $^{111}$In-desferrioxamine-PE is added to cholesterol and lecithin to prepare liposomes as described below.

Example 3

Glycosylated and Mannosylated Lipid Carriers, e.g., Liposomes

Glycosylated liposomes are prepared by linking liposomes to a hydrophobic anchor N-glutarylphosphatidylethanolamine (NGPE), which have been previously derivatized with the sugar residues. Mannosylated lipids can be purchased commercially from Sigma. The carboxylic groups of NGPE are first activated by water soluble 1-ethyl-3 (3-dimethylaminopropyl) carbodiimide (EDC) to which ethylenediamine is then added to provide free amino groups. Thiolated galactose and mannose residues are then incorporated onto the amino groups of the ethylenediamine by the method of Lee et al. (Lee, Y. C. et al. (1976) Biochem. 15:3956-3963).

Example 4

Iron Chelator and Galactosylated and Mannosylated Lipid Carriers, e.g., Liposomes N-glutarylphosphatidylethanolamine (NGPE) (0.075 mg) is dissolved in 2-(N-morpholino) ethanesulfonic acid hemisodium salt (MES) buffer (0.016M octylglucoside in 50 mM MES). After addition of 0.6 mg 1-ethyl-3-(3-dimethylaminopropyl) carbodiimide (EDC) the resulting mixture is incubated at room temperature for 5 minutes. Ethylenediamine (100 μM) is then added to the activated NGPE and the solution kept at pH 5.0 by the addition of 1 N HCl solution. The reaction is allowed to proceed overnight with stirring and the solution is dialyzed against distilled water. Sugar residues are incorporated onto the amino groups of ethylenediamine-coupled NGPE by using 2-imino-2-methoxyethyl 1-thiogalactoside or 1-thio-mannoside to obtain galactosylated and mannosylated NGPE.

Liposomes are prepared by reverse phase evaporation technique (Ashwell, G. (1974) Adv. Enzymol. 41:99-128) as previously described and outlined above. The aqueous phase containing desferrioxamine mesylate and either galactosylated or mannosylated NGPE are added to the solubilized lipids. The two phases are vortexed for formation without emulsion. Liposomes are obtained by evaporating the organic phase under a partial vacuum produced by a water aspirator on a rotary evaporator. The resulting liposomes are extruded through Nucleopore™ polycarbonate membrane filters. The nonliposomal desferrioxamine can be removed by a Sephadex G-50 spin-column and centrifugation as described above.

Example 5

Iron Chelator and Cationic Tagged Lipid Carriers, e.g., Liposomes

Positively charged (cationic) liposomes are prepared according to Caride and Zaret (Caride et al. (1977) Science 1989:735-738), the entire disclosure of which is hereby incorporated herein by reference for all purposes. Cationic liposomes are prepared using lecithin, cholesterol and stearylamine (80:10:10 molar ratios). Incorporation of desferrioxamine into the cationic liposomes is as previously described. Trace amounts of In-111 DTPA-PA are added to radiolabel liposomes. Other suitable methods of making cationic liposomes using selected cationic lipids will be readily selected by the person of ordinary skill in the art, given the benefit of this disclosure.

Example 6

Preparation of Fluorescein Desferrioxamine

An aliquot of 120 mg of desferrioxamine and 233.64 mg of fluorescein isothiocyanate (FITC) are mixed in 50 mL of 0.1 M sodium carbonate pH 9.5. A molar ratio of 3:1 of FITC:desferrioxamine is used as described in Hentz et al. (1997) Anal. Chem. 69:4994-5000. The reaction mixture is wrapped in aluminum foil to avoid light exposure and allowed to react for at least 24 hours at room temperature. To separate fluorescently labeled desferrioxamine from free fluorescein and free desferrioxamine, the mixture is separated using a P-2 column (Bio-Rad) equilibrated in saline and samples are eluted in 2 mL fractions. The fluorescein-desferrioxamine is eluted in the void volume of the column. The first peak is collected and used for preparing fluorescein-desferrioxamine, desferrioxamine, and rhodamine liposomes.

Example 7

Preparation of Rhodamine Labeled Liposomes Containing Unlabeled Desferrioxamine and Rhodamine Labeled Liposomes Containing Fluorescein Labeled Desferrioxamine An aliquot of 75 mg 1-α-phosphatidylcholine (20 mg/mL chloroform, Avanti Lipids) is added to a 50 mL round bottom flask. Forty-five mg of cholesterol (cholestin-3β-ol) is added to the solution of phosphatidylcholine. To this mixture is added 373 μL of 2 mg/mL 1,2 dipalmitoyl-sn-glycero-3-phosphaethanolamine-N-(lissamine rhodamine β sulfonyl) (Avanti Lipids). The mixture is stirred by vortexing until thoroughly mixed. The mixture is then evaporated with a rotary evaporator set at 42° C. for 1 hour at 160 rpm. One hundred and twenty mg of desferrioxamine is dissolved in 20 mL of physiological saline and then added to the evaporated lipids in the rotary evaporation flask. To this mixture is added 10% (vol/vol) of fluorescein-desferrioxamine (approximately 2 mL). The mixture is stirred vigorously with a vortex mixer. The unilamellar vesicles, i.e. liposomes, are chromatographed using multiple columns of PD-10 (Pharmacia, Sephadex-G25) for column centrifugation as described above. The liposomes that are eluted in the eluate are pooled and extruded at least 5 times each serially through 0.8, 0.45, and 0.22 micron diameter Nucleopore™ filters. A total of 120 mg of lipid is collected in a total of 20 mL of physiological saline. Assuming a loss of 20% in the column centrifugation, the final lipid concentration in the 20 mL sample is approximately 96 mg/mL of desferrioxamine and 9.6 mg of fluorescein-desferrioxamine.

To prepare rhodamine liposomes with non-fluorescent desferrioxamine, the fluorescein-desferrioxamine is not included in the above formulation and the remainder of the protocol remains the same.

Example 8

Analysis of Iron-Overloaded Animals Used in the Following Experiments

Eighty Hartley Guinea Pigs weighing 350-400 grams of both sexes were purchased from Harlen or Elm Hill Breeding Farm. Iron dextran was administered at 1.5 g Fe/kg body weight intraperitoneal three times a week for four weeks. Animals were divided into groups to receive iron chelator without lipid carrier and chelator with lipid carrier as described herein. Desferrioxamine was given intramuscularly twice a day daily for a total concentration of 20 mg/kg daily for five days a week for four weeks. Intravenous lipid associated chelator was given intravenously three times a week at 0.6 mg.

Iron-overloaded animals were sacrificed and various organs were analyzed. The pattern of changes in the organs of all the iron-overloaded animals studied were similar with slight differences in severity. In the livers, there was a mild to moderate Kupffer cell hyperplasia in hepatic sinusoids. The Kupffer cells were distended with black globular material (Hematoxylin and Eosin) that was iron positive (Perl's iron stain). The Kupffer cells were clumped (granulomas) in those animals having moderate hyperplasia. The clumping was random and often associated with degeneration, necrosis, and replacement of hepatocytes. Rarely, lymphocytes were admixed. Hepatocytes also contained small amounts of iron positive material detected with special stains.

The hearts were characterized by cellular infiltration of macrophages containing iron. These cells were present in the epicardium and myocardium (perivascularly and in the interstitium) and in the adipose tissue at the base of the heart and perivascularly around the pulmonary vessels.

This model of iron overload reflects the human condition and is suitable for testing the iron chelator delivery system described herein. Guinea pigs have been treated with the non-lipid associated chelator (8 mg/day 5 days per week) and the lipid-associated chelator (8 mg/day three days per week). In two animals, after only three injections of the lipid associated chelator, the color of the eyes and ears were restored to that seen in non-overloaded Guinea Pigs.

Example 9

Targeted Delivery of Iron Chelator System

Targeted delivery of iron chelator delivery systems comprising, for example, desferrioxamine and liposomes, can be shown by comparing the delivery of the liposomes in normal animals with the delivery of the liposomes in animals with iron-overload. Radiolabeled liposomes can be used to quantify the localization into targeted tissues and, for example, the effect on heart function in particular arrhythmogenesis and contractile dysfunction can be evaluated.

The Heart: Iron chelator delivery systems comprising, for example, desferrioxamine and liposomes, for targeting the heart include placing one or more cationic groups, or in certain cases anionic groups, on the liposomes which might adversely affect the conduction system of the heart. Injection of the desferrioxamine and liposome system can be done intra-venously. Caride and Zaret in 1977 (Caride, W. J. (1977) Science 1989:735-738) showed that positively charged liposomes can be targeted specifically for acute myocardial ischemia or infarction in an experimental model. When uptake was compared to regional myocardial blood flow, it was observed to have an inverse correlation to the liposome distribution. Negatively charged (anionic) liposomes, however, distributed relative to blood flow. Myocardial blood flow was observed to have an inverse correlation to the liposome distribution. Since there is myocardial involvement in iron toxicity, there is a possibility of damage to the myocardium. Cationic or anionic liposomes may also localize preferentially in iron-overloaded myocardium. Another approach would be to tag the iron chelator delivery system with antibodies targeted to cardiac specific endothelial cells, vascular smooth muscle cells, matrix proteins, receptors, and/or myocardial cells.

The Liver: Carbohydrate receptors in the liver, such as asialoglycoprotein receptors on the hepatocytes and mannose receptors on Kupfer cells and endothelial cells, allow selective targeting of this organ (Ashwell, G. (1974) Adv. Enzymol. 41:99-128), (Ashwell, G. (1982) Ann. Rev. Biochem. 51:531-554), (Fallon, R. J. (1989) Adv. Drug Del. Rev. 4:49-63), (Gordon, S. (1989) Adv. Drug Del. Rev. 4:27-47), (Meijer, D. K. F. (1989) Phar. Res. 6:105-118) by desferrioxamine-encapsulated vesicles. Vesicles, e.g. liposomes, can be utilized as carrier molecules because of their low immunogenicity, their relative biocompatability, and their drug encapsulation efficiency. With glycosylated vesicles the targeting efficiency to the liver can be increased.

Example 10

Determination of the Toxicity of the Iron Chelator Delivery System

Toxicity in the administration of the iron chelator delivery system, e.g., desferrioxamine combined with a lipid carrier, e.g., a liposome, can be tested in animal models. For example, two species of normal animals and iron-overloaded animals (e.g., the guinea pig) can be compared. One group of animals receives the delivery system comprising desferrioxamine and a lipid carrier, e.g., desferrioxamine-encapsulated within a vesicle, and another group receives similar lipid carrier without the desferrioxamine. Animals are monitored for cardiac arrhythmias via electrocardiogram once a week. Heart function is determined with echocardiography at the same time that electrocardiograph recordings are made at one and at 24 hour intervals post-injection followed by weekly monitoring for up to 6 weeks. Full necropsy is performed with special attention to harvesting the liver and heart. In humans, the infusion of the iron chelator delivery system, e.g., desferrioxamine combined with a lipid carrier, desferrioxamine encapsulated within a liposome, etc. is estimated to take between about 20-30 minutes to about 3 hours at a rate of about 50 cc/hour in normal saline (0.9% NaCl). Repeat treatments typically would occur over a 3-6 week interval. Based on this predicted course of therapy, cardiac and liver functions are monitored in the animals after one hour, 24 hours, and at weekly intervals up to ten weeks.

Local skin irritation at the infusion site is a complaint of the current formulation of desferrioxamine. Irritation should not occur, or should be reduced, with the use of the present iron chelator delivery system, e.g., desferrioxamine encapsulated within a vesicle. Animal body weight, serial hematocrits, blood iron levels, and ferritin plasma levels are determined on individual animals. Blood samples are analyzed with full differential including creatinine and complete CBC to check for agranulocytosis as seen with deferiprone. Analysis of liver enzymes including aspartate aminotransferase (AST) or serum glutamic oxaloacetic transaminase (SGOT), alanine aminotransferase (ALT) or serum glutamic pyruvic transaminase (SGPT), alkaline phosphatase, blood urea nitrogen (BUN), etc. is performed once a week. Urine excretion or iron is measured in iron-overload animals by atomic absorption spectroscopy.

Dosing range, safety, and toxicity studies in normal animals, as well as, quantification of any toxicity seen in the liver, heart, gastrointestinal tract, kidney, and at the injection site is important. At the time of full body necropsy tissue weights and gross appearance is recorded. The heart and liver are stored in 10% phosphate buffered formalin. Other body organs are also stored in 10% buffered formalin for future light miscroscopy, or special staining. Prussian blue iron stain is applied to liver and heart samples. Quantitative analysis using a point counting technique and semi-quantitative technique using a scale of ±4 can be used. It is preferred, but not required, that all measurements are made by a single observer to increase consistency.

Flame photometry atomic absorption spectroscopy measurements are carried out on fresh or lyophilized liver and heart with either normal iron depot or iron-overload with or without the present iron chelator delivery system, e.g., desferrioxamine encapsulated within a liposome, administered. Normal animals treated with the targeted iron chelator delivery system, e.g., desferrioxamine encapsulated within a liposome, and non-treated normal animals are compared for possible reduction in normal iron levels. Iron deficiency can in itself result in cardiomyopathy. Similar studies would be applied to Mongolian gerbils and rats with iron-overload and thalassemic rats.

Example 11

Sprague Dawley rats (n=130) were obtained from Charles River Laboratories and were iron overloaded by twelve week administration of iron in the feed. The rats were divided into the following groups:
 (i) overloaded (O),
 (ii) liposomes injected (OL),
 (iii) overloaded animals with liposome entrapped desferrioxamine (OLD), and
 (iv) overloaded with desferrioxamine (OD).

Controls were similarly set up in to four groups of 30 (control (C), control with liposome injected (CL), control with lipsome entrapped desferrioxamine (CLD), and control overloaded with desferrioxamine (CD). The animals received an injection once a week for three months. Liver iron content was measured at the end of the study. FIG. 3 demonstrates iron content and hepatic index.

Figure 4:
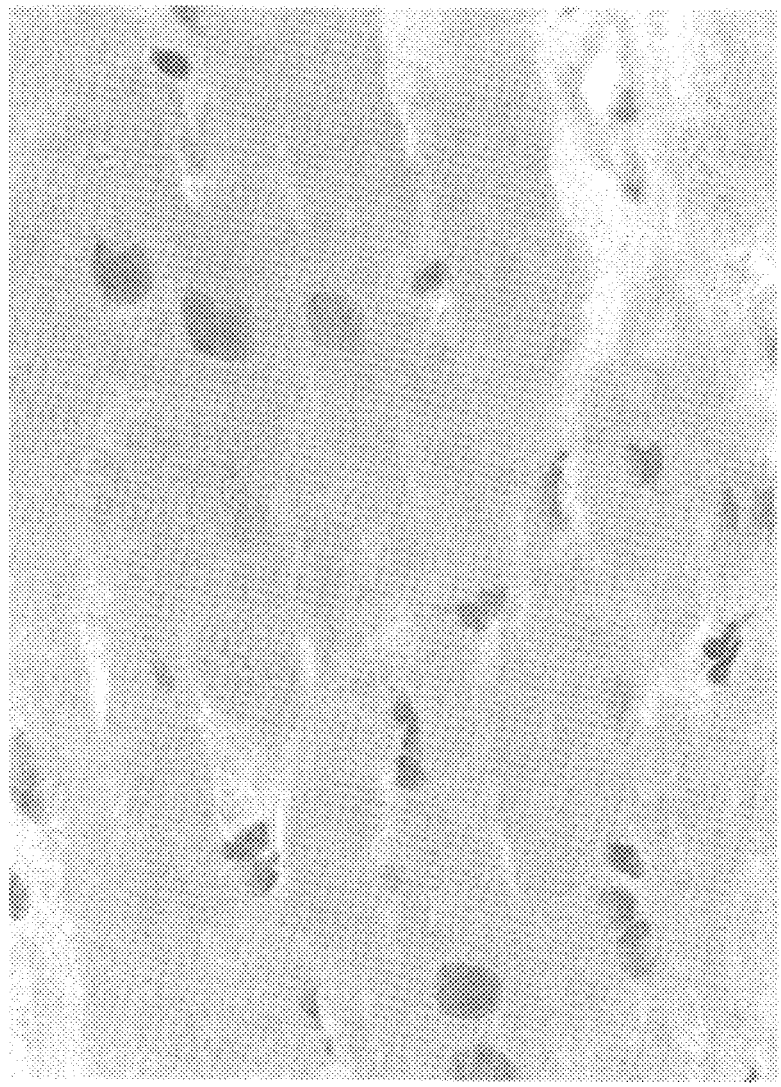
FIG. 4 is hematoxylin and eosin (H & E) stain of myocytes showing brown-black pigmentation of the myocytes with iron overload, in accordance with certain examples.
Figure 5:
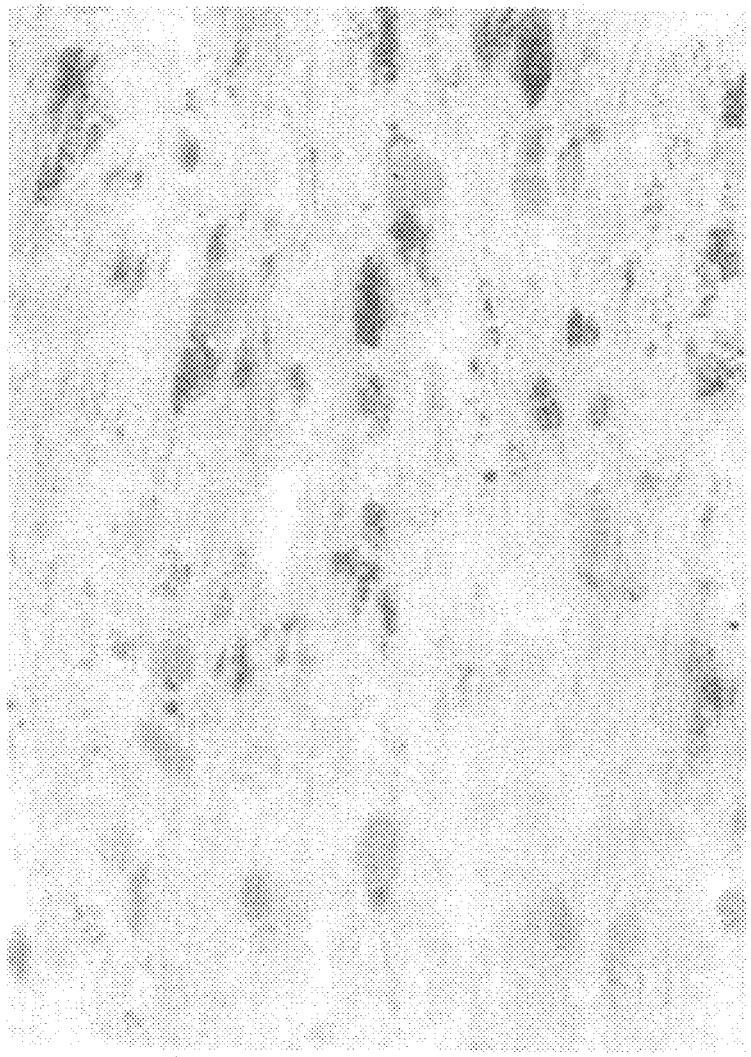
FIG. 5 is a Prussian blue stain of myocytes showing iron pigmentation, in accordance with certain examples.
Figure 6:
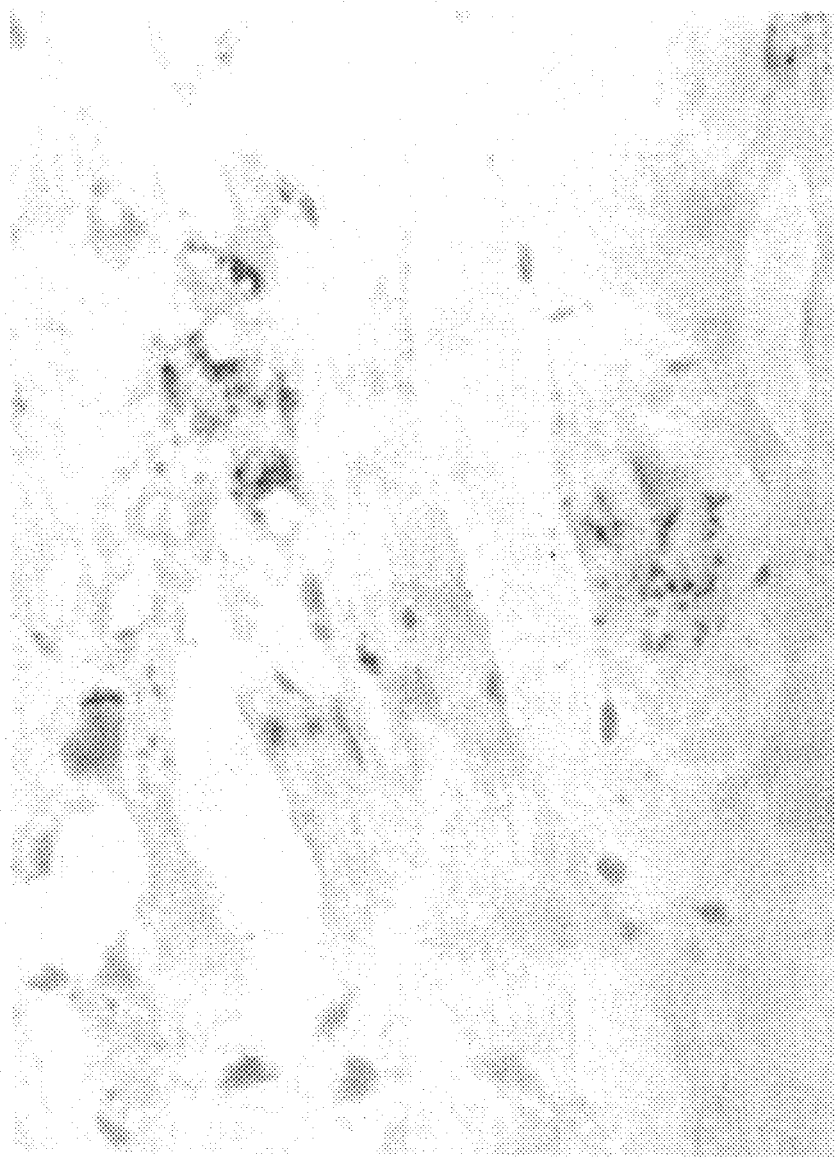
FIG. 6 is a Prussian blue stain of myocytes after treatment with liposome entrapped DFO, in accordance with certain examples.

All control groups were pooled as there were not significant differences between the groups of normal non-treated controls. Range for iron was 35-150 µg/gram dry weight (human assay lab). A hepatic index of 1.0 is normal and results of 1.0-1.9 are described as nonspecific iron accumulation (human standards). Neither liposomes nor desferrioxamine (DFO) had toxic effects in control rats. No respiratory or allergic side effects were noted with intravenous liposome entrapped DFO injection. Histopathological analysis of the site of injection did not reveal any adverse effect or inflammation. Animals receiving liposome entrapped DFO had less liver and myocardial content of iron compared to liposome alone or DFO treated animals. This data is consistent with removal of iron by the targeted iron chelator delivery system disclosed here. FIGS. 4 and 5 show myocardial tissue from rat with iron overload. FIG. 4 shows hematoxylin and eosin (H & E) staining demonstrating brown-black pigmentation of the myocytes. FIG. 5 shows Prussian blue staining showing the pigmentation to be iron. FIG. 6 confirms that after liposome entrapped DFO treatment for a relatively short period of time there is a significant decrease in iron in the myocardium with Prussian blue stain. This data is consistent removal of iron using the iron chelator delivery system disclosed here.

Cardiac catheterization of the heart revealed no systolic dysfunction in rats that were iron overloaded (see FIG. 7A showing measurements of systolic pressure LVP (open bars of FIG. 7A) and LV end-diastolic pressure (closed bars of FIG. 7A)). FIG. 7B shows measurements of LV+dP/dt (open bars of FIG. 7B), and −dP/dt (closed bars of FIG. 7B). Further analysis of myocardial function using sonomicrometry revealed diastolic dysfunction in iron overloaded rats after 12 weeks of receiving iron in the feed. On echocardiography there was no sign of overt heart failure with LV enlargement. FIG. 7C shows the measurement of the time constant of relaxation (tau) in adult rat hearts from Sprague Dawley iron overloaded and non-iron overloaded rats (*$P<0.05$ compared with non-overloaded).

Example 12

Figure 8:
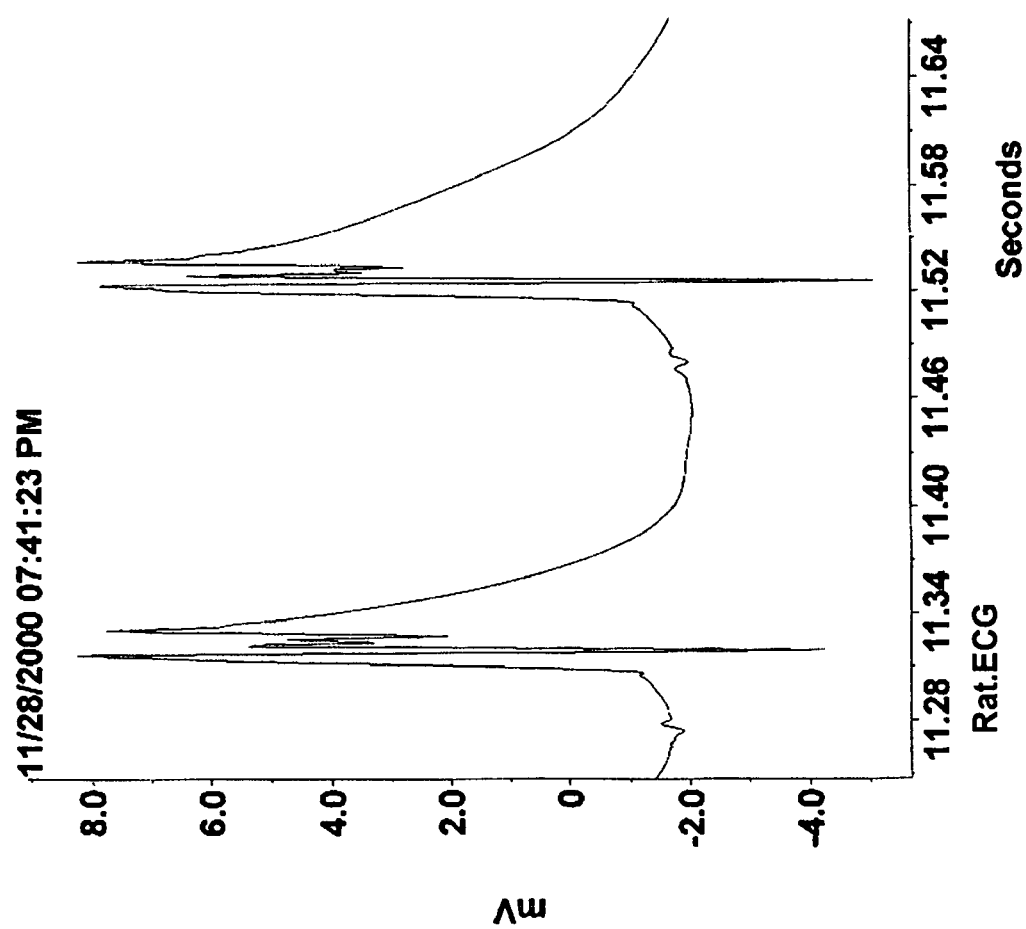
FIG. 8 is an ECG showing ST segment elevation in rats with iron overload, in accordance with certain examples.
Figure 9:
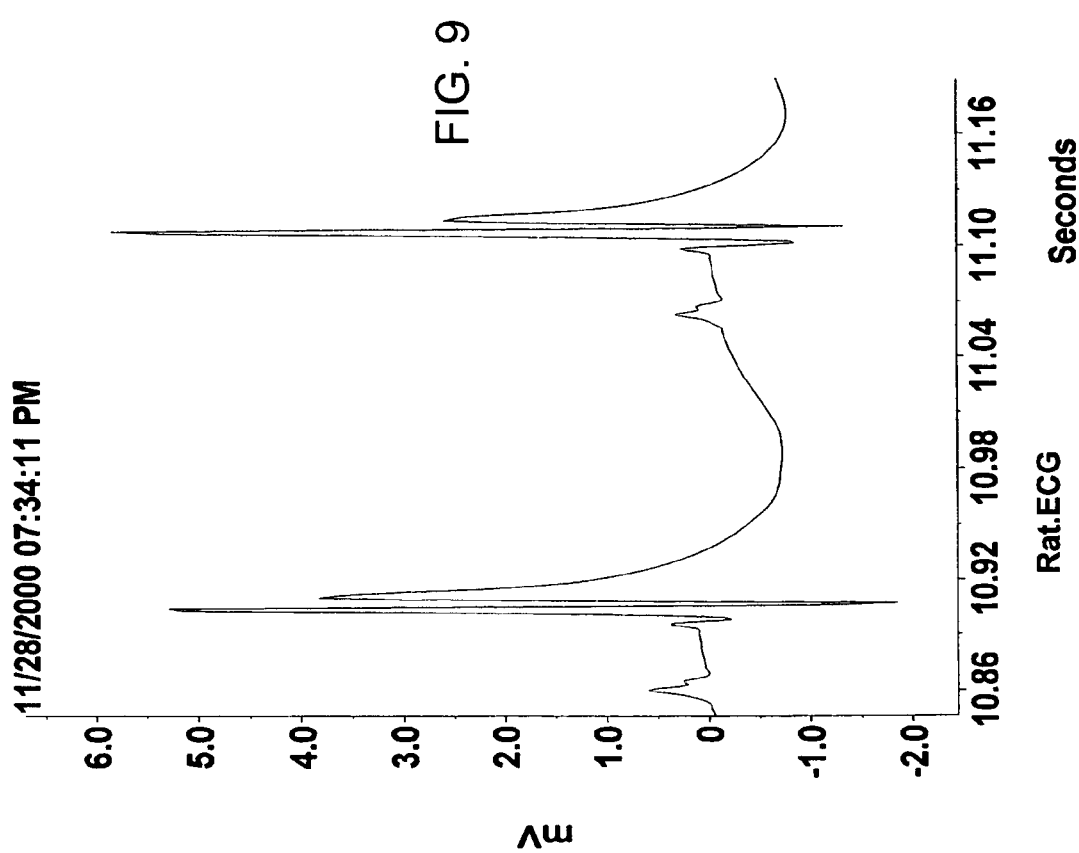
FIG. 9 is an ECG showing restoration of the normal QR interval, PR interval and restoration of normal QRS complex in rats after treatment with positively charged liposomes containing DFO, in accordance with certain examples.

Cationic tagged liposomes were prepared with entrapped desferrioxamine using the methods described above. The liposomes were delivered using catheter base delivery to provide higher concentrations of the liposomes within the myocardium. Delivery of the liposomes was accomplished using an open and closed chest approach that had been developed to deliver transgenes to the heart. This approach resulted in higher concentrations of the liposomes in the heart and greater iron chelation within the heart. Iron overloaded animals showed signs of ischemia (see ST segment elevation in rat with iron overload in FIG. 8). Treatment with cationic liposomes containing DFO resulted in restoration of the normal QR interval, PR interval and restoration of normal QRS complex. ECG signs of ischemia were also diminished or restored to near normal (see FIG. 9).

Example 13

Figure 10:
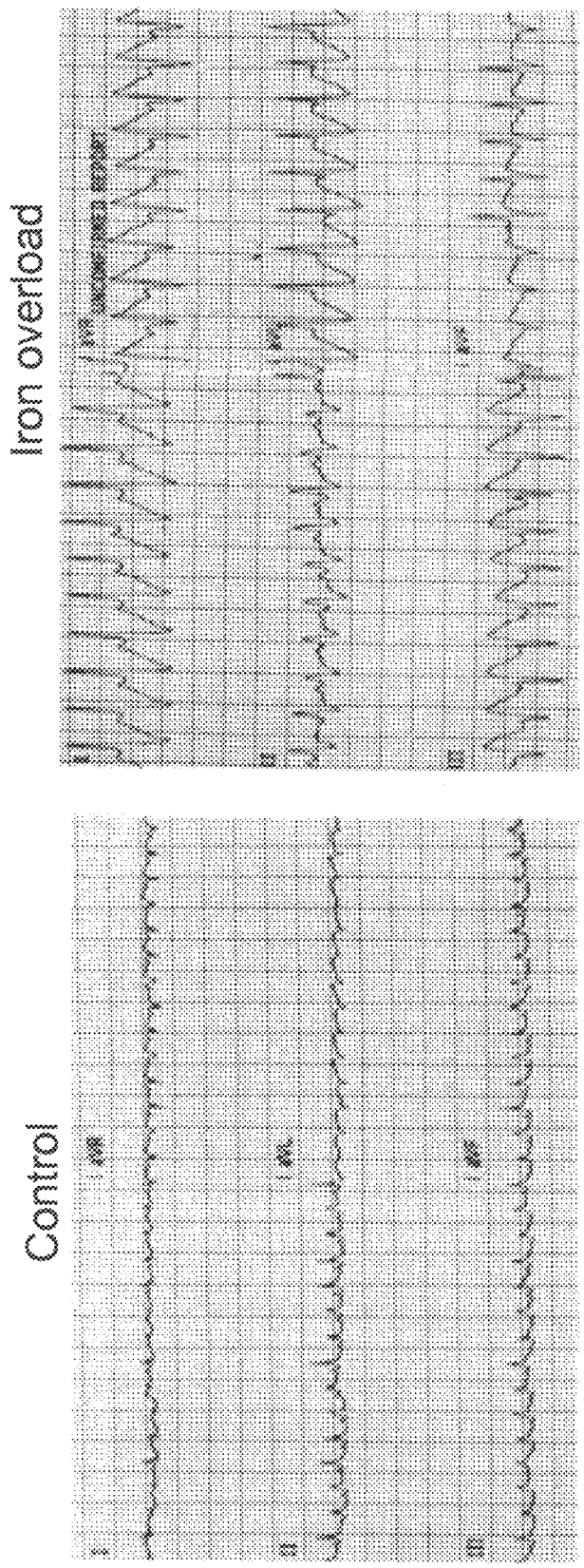
FIG. 10 shows an ECG of a rat with iron overload, in accordance with certain examples.
Figure 11B:
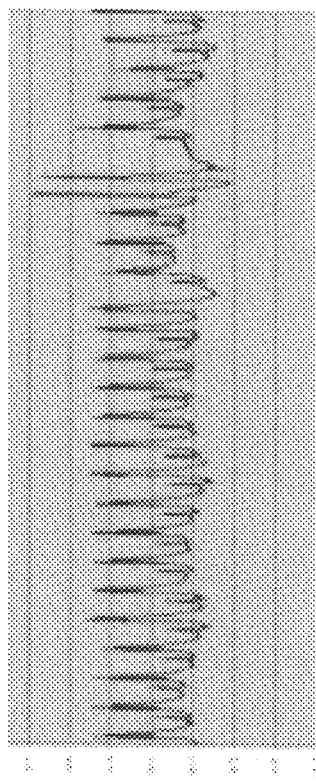
FIGS. 11A and 11B show an ECG of iron overloaded rats before and after administration of liposomes with entrapped desferrioxamine, in accordance with certain examples.
Figure 11A:
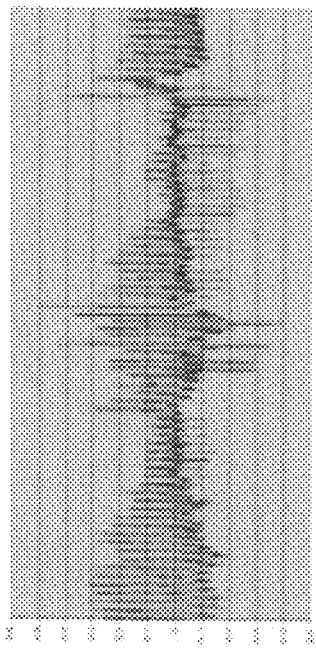

6 lead ECGs from iron-overloaded rats (see Example 10) were recorded following iron loading. As shown in FIG. 10, the ECG from the rat with iron overload has elevated voltage amplitude, ST depression, and left axis deviation. In addition, liposome+DFO administration significantly reduced ventricular arrythmia (40±2% vs. 10±3% $p<0.001$). Also, ventricular tachycardia is reduced with liposome entrapped DFO delivery to the heart (see FIGS. 11A and 11B).

Example 14

Figure 12:
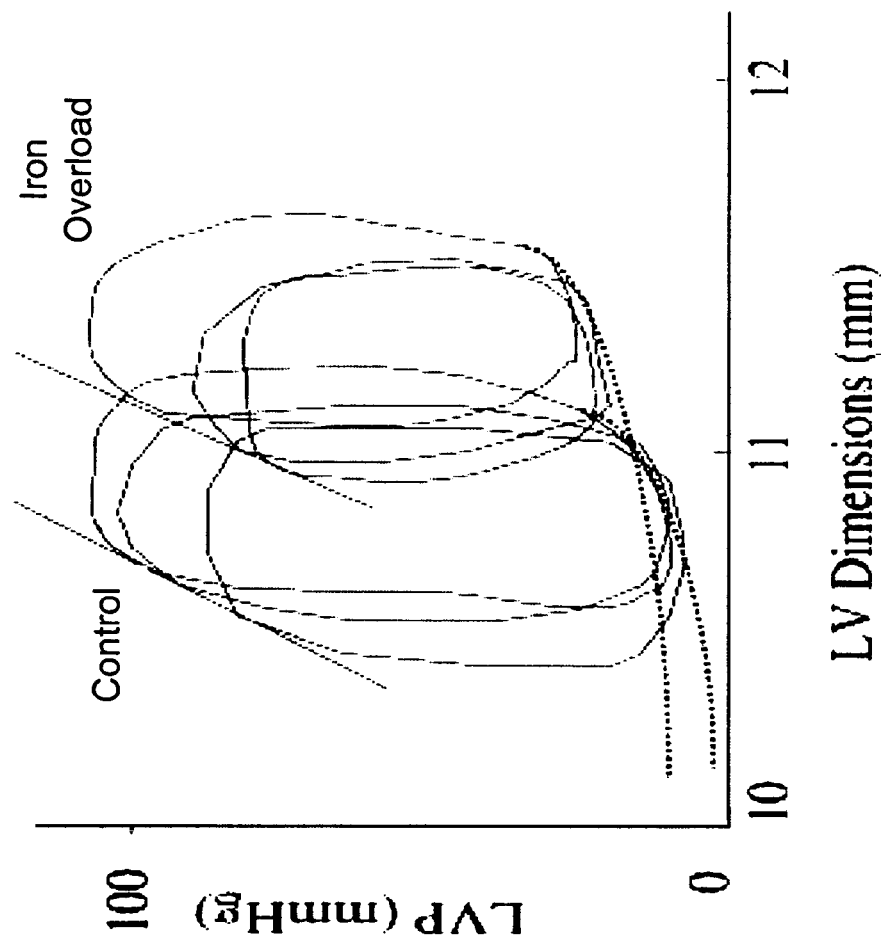
FIG. 12 is a graph of left ventricular pressure (LVP) versus left ventricle dimensions, in accordance with certain examples.

To characterize the hemodynamics of the rat hearts, left ventricular pressures were measured using a high fidelity manometer (Millar catheter) placed into the left ventricle through the apex of the heart in a ventilated rat (see FIGS. 7A and 12). To further define ventricular function, pressure-dimension analysis was performed in the rats using piezoelectric crystals placed at the base of the heart in a cross-sectional fashion. To alter loading conditions, the inferior vena cava was clamped in the open chested animals thereby reducing ventricular volume. This method has allowed for the calculation of the maximal end-systolic pressure dimension relationship using a series of pressure-dimension relationships under varying pre-load conditions. As shown in FIGS. 7A and 12, the −dP/dt were significantly reduced in rats with iron overload and diastolic stiffness was increased after six months of iron overloading. This result is consistent with increased diastolic stiffness observed in humans patients with iron overload.

Example 15

Determination and Comparison of the Biological Half-Life of Iron Chelator Delivery Systems Iron-overloaded rats were given iron chelator delivery systems comprising, for example, desferrioxamine and liposomes. Iron blood levels were measured before and after injection. Pharmacokinetic studies were performed in both iron-overloaded and normal animals with radiolabeled liposomes. One group of animals also received the standard formulation of desferrioxamine injected over a 24 hour period via a minipump similar to the standard procedure for humans receiving the compound. The localization of desferrioxamine was radiolabeled for imaging and quantification of organ localization.

Imaging: Male and female rats age 10-12 weeks were injected intravenously with 100 µCi $^{111}$In-desferrioxamine liposomes (4 µCi/µmol lipid, fluid liposome type) or 100 µCi free $^{111}$In-desferrioxamine. The amount of desferrioxamine to be injected was determined in experiments without radiolabeling using fluorescent labels. Rats were anesthetized (halothane-nitrous oxide-oxygen) and placed prone on a single head camera equipped with a parallel hole, medium energy collimator to image the entire body with special focus on liver, kidney, brain, and heart. Symmetric 20 percent windows were focused for both 173 and 247 keV energy peaks. Images (100,000 counts/image) were obtained and stored in a 256×256 matrix. The scintigraphic results were analyzed by drawing regions of interest. Images were obtained at 0.5, 1, 2, 4, 6, 24, 48, 72, 96, and 144 hours after injection of $^{111}$In-desferrioxamine-liposomes and free drug (five rats per time point).

In at least one experiment, the amount of liposome-entrapped desferrioxamine was found to be highest in the liver and had a longer biological half-life than the iron chelator alone.

Pharmacokinetics/Biological Half-Life Determinations: Pharmacokinetic studies are performed in both iron overloaded and normal animals with radiolabeled liposomes. Pharmacokinetic parameters are calculated using the curve fitting program KINFIT. Values of $^{111}$In-desferrioxamine in blood versus time are fitted by a model for extravesicular administration and two compartments without lag time. The half-life of blood levels of liposome-entrapped desferrioxamine is determined.

Example 16

Toxicity Study in Normal Animals

Safety studies were performed in six 200 gram female rats. Three rats were injected via tail vein with 2 mL of iron chelator delivery systems comprising, for example, Desferrioxamine and liposomes, (10 mg). Three additional animals received the liposomes without desferrioxamine. No toxicity or morbidity was noted up to ten days post-injection. There was no irritation noted at the injection site. Blood chemistry values before and after liposome infusion (with and without desferrioxamine) were not significantly different (see FIG. 13).

Rats were anesthetized and allowed to breathe spontaneously during fluid filled catheter recordings of left ventricle (LV) pressure. Closed chest LV systolic pressures were 180±4 mm Hg before intravenous injection of the desferrioxamine-encapsulated liposomes versus 181±4 after injection. At one hour after injection the LV systolic pressure was 175±5 mm Hg (p>0.05).

Simple semi-quantitative analysis of tissues from animals receiving the liposomes without desferrioxamine and liposomes with desferrioxamine (i.e., liver and heart) stained for iron revealed no differences by light microscopic examination.

Example 17

Histological Findings of Rats Injected with Rhodamine Labeled Liposomes Containing Fluorescein Labeled Desferrioxamine Forty-two rats were injected with 2 cc of rhodamine labeled liposomes containing 0.6 mg/mL of desferrioxamine labeled with fluorescein. Heart, liver, brain, and both kidneys were harvested. Tissues were frozen for later fluorescent imaging or stored in buffered formalin, sectioned, and stained with hematoxylin and eosin and counter stained with Masson's trichrome. Histological reading by a board certified laboratory veterinary pathologist reported no remarkable change. No morbidity or toxicity was noted up to ten days post-injection. There was no irritation noted at the injection site. An additional group of animals were euthanized at 30 minutes, 1 hour, and 24 hours post-injection of desferrioxamine labeled with fluorescein entrapped in liposomes labeled with rhodamine. Histological analysis showed fluorescent labeling in the liver of liposomes and of desferrioxamine in the Kupffer cells at the 30 minute time point. Discrete localization was seen up to two hours post-injection. The 24 hour time point demonstrated homogenous fluorescence due to re-distribution of the lipids in the liposomes and desferrioxamine. There was no detected organ damage. No signs of toxicity were noted in any of the experiments at the organ level or clinical presentation. The brain was examined for histological changes as lipids can easily cross the blood brain barrier. No indication was found of liposome distribution in the brain, heart, or kidney.

Example 18

Biodistribution of the Iron Chelator Delivery System

Rats are injected intravenously with 10 µCi $^{111}$In-desferrioxamine liposomes or 10 µCi free $^{111}$In-desferrioxamine at a total dose of 25 µmol desferrioxamine targeted (injection volume 0.5 mL). At predefined time points after injection, rats receive an overdose of pentobarbitol and blood is obtained by cardiac puncture. The following tissues are dissected: injection site; muscle; lung; spleen; kidney; liver; heart; and brain. These tissues are also weighed and the activity measured in a shielded well-type gamma counter. To correct for physical decay and to calculate uptake in each organ as a fraction of the injected dose, aliquots of the injected dose are counted simultaneously. The results of this study are shown in FIGS. 14-27. With general reference to FIGS. 16-27, following the injection of radiolabeled desferrioxamine, radioactivity is observed in the kidney and the spleen. Lung, spleen, blood, skeletal muscle, brain, heart, and liver are also radioactive. No radioactivity is observed in the brain, indicating that the iron chelator delivery system does not cross the blood brain barrier. As the radioactivity in the blood drops over time, the liver localization of the radioactive iron chelator delivery system increases. Subsequently, the chelated desferrioxamine is removed from the liver. Radiolabeled chelator without liposomes was quickly eliminated from the animals and did not accumulate in the tissues, especially the liver and tracked blood distribution. This data is consistent with prolonged delivery of iron chelator using the iron chelator delivery system disclosed here.

Figure 14:
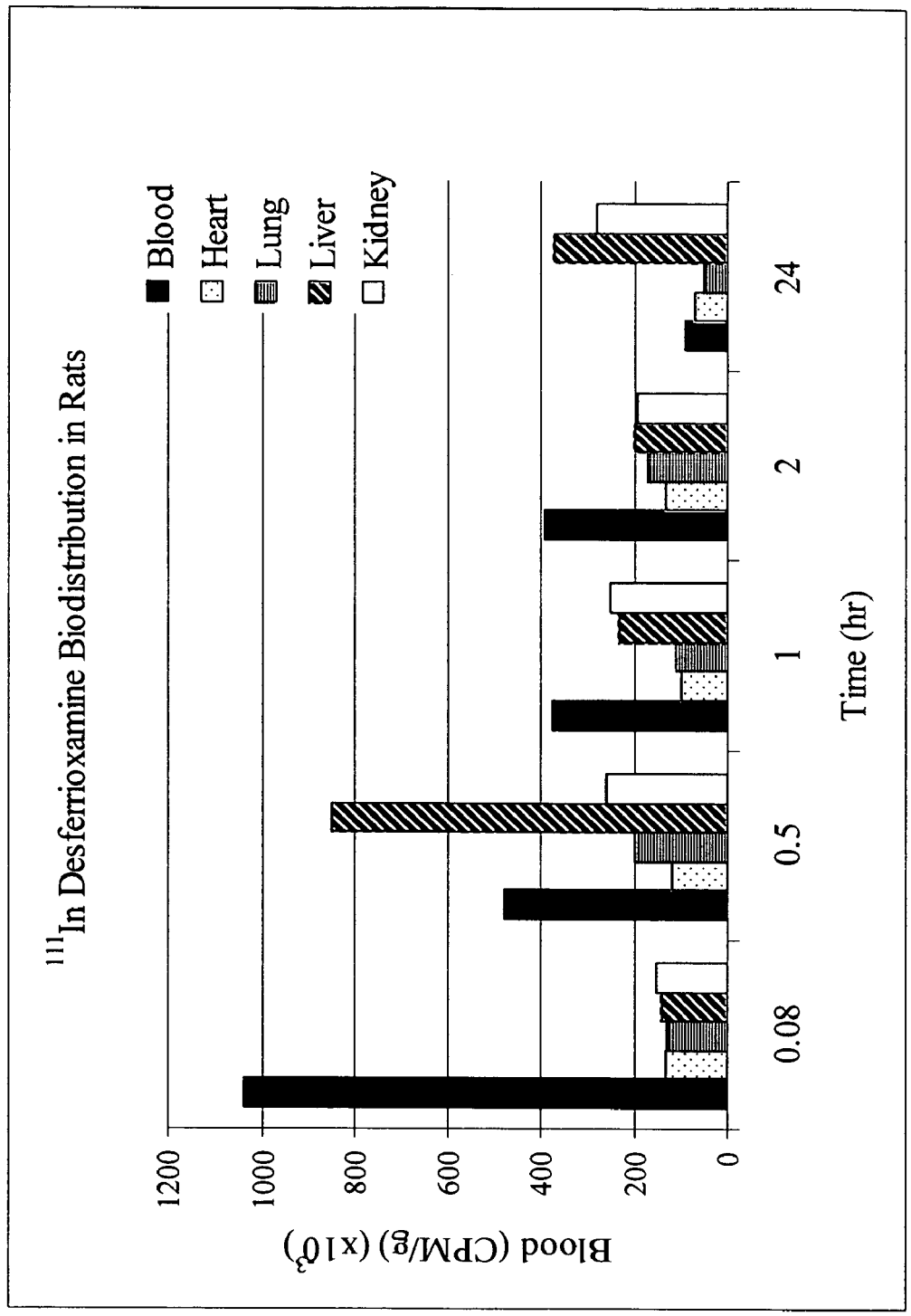
FIG. 14 is a bar graph showing counts per minute/gram of tissue versus time in selected tissues or organs including blood, heart, lung, liver and kidney, in accordance with certain examples.

Referring specifically now to FIG. 14, at 0.08 hours following injection, the $^{111}$In-desferrioxamine is located predominantly in the blood with small amounts in the heart, lung, liver and kidneys. At 0.5 hours following injection, the amount of $^{111}$In-desferrioxamine in the blood has decreased while the amount of $^{111}$In-desferrioxamine in the liver has increased over 4-fold. As the $^{111}$In-desferrioxamine is removed from the body, the levels of $^{111}$In-desferrioxamine in the blood decrease. In particular, 24 hours after injection, the level of $^{111}$In-desferrioxamine in the blood has decreased over 10-fold. $^{111}$In-desferrioxamine was also found in the heart, lung and kidneys but to a lower extent than the levels in the liver. This data is consistent with prolonged delivery of iron chelator by using the iron chelator delivery system disclosed here.

Figure 15:
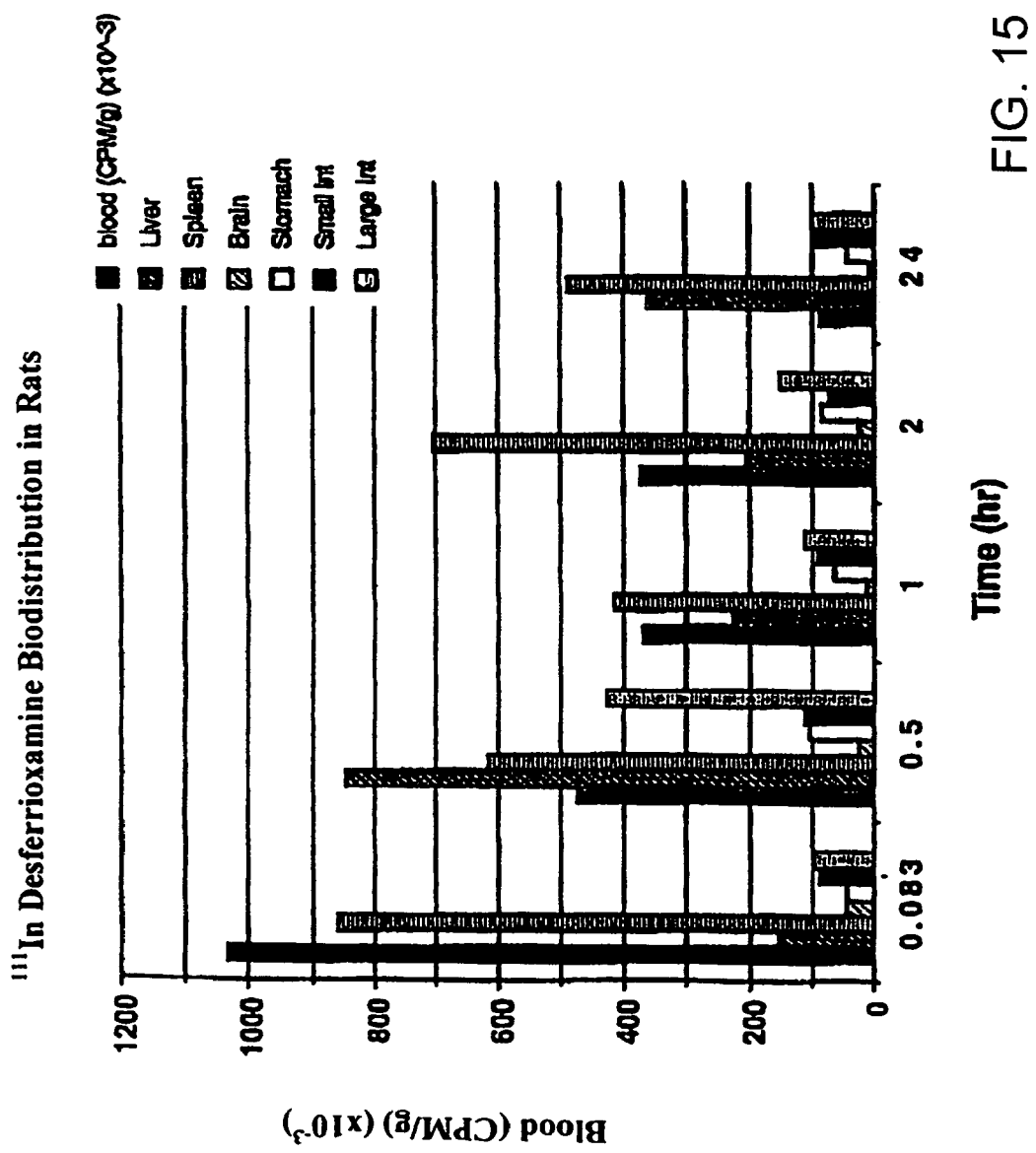
FIG. 15 is another bar graph showing counts per minute/gram of tissue versus time in selected tissues or organs including blood, liver, spleen, brain, stomach, small intestine and large intestine, in accordance with certain examples.

Referring specifically now to FIG. 15, at 0.5 hours following injection, the amount of $^{111}$In-desferrioxamine redistributes from the blood to the liver and spleen. At 24 hours following injection, the $^{111}$In-desferrioxamine level in the spleen remains high relative to the levels in the other tissues or organs. The level of $^{111}$In-desferrioxamine in the blood and the brain remains relatively low throughout the 24 hour period following injection. This result is consistent with no or minimal crossing of the $^{111}$In-desferrioxamine liposomes across the blood-brain barrier. The levels in the small intestine and the large intestine are 2.5-3 fold less than those found in the spleen. The results are consistent with preferential uptake/ delivery of the $^{111}$In-desferrioxamine by the liver and spleen.

Figure 16:
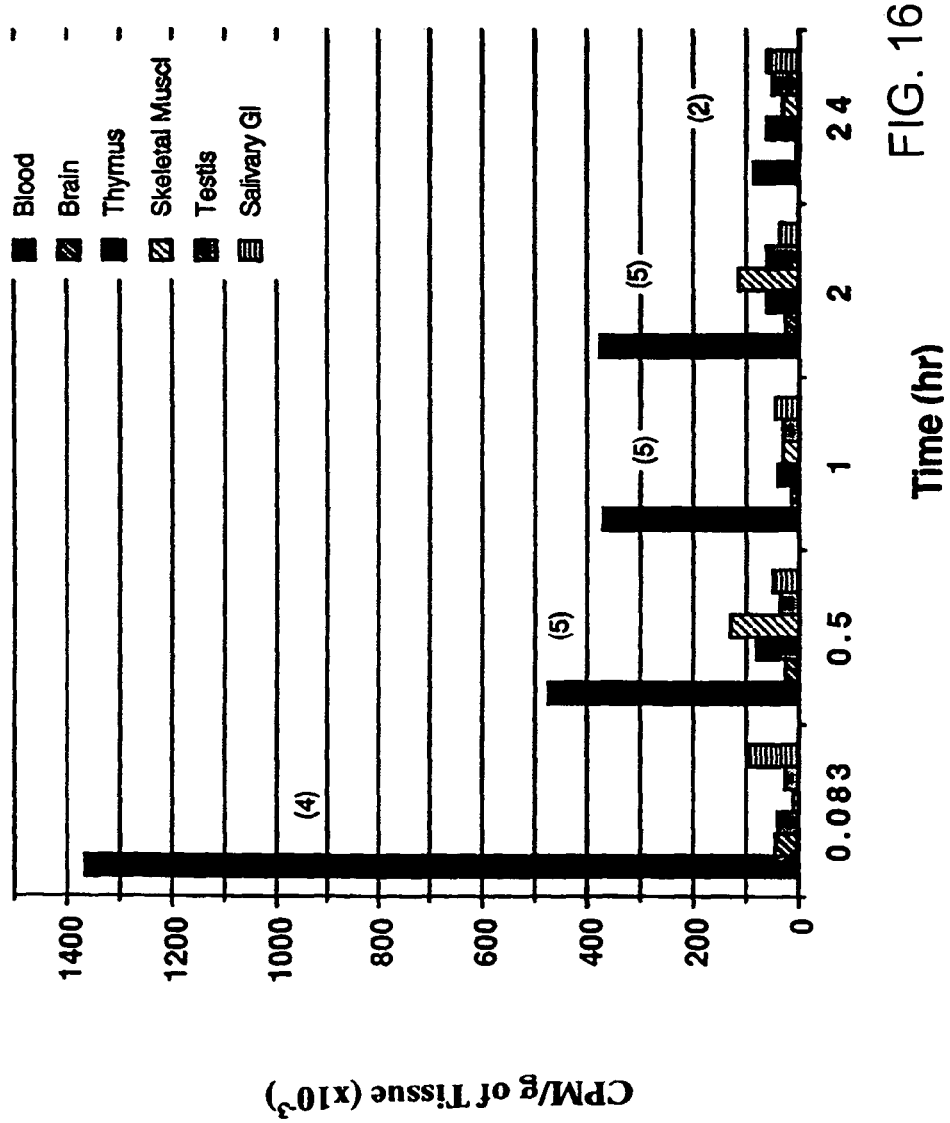
FIG. 16 is an additional bar graph showing counts per minute/gram of tissue versus time in selected tissues or organs including blood, brain, thymus, skeletal muscle, testis and salivary glands, in accordance with certain examples.

Referring specifically now to FIG. 16, at 0.5 hours following injection, the amount of $^{111}$In-desferrioxamine present in the brain, thymus, skeletal muscle, testis and salivary glands remains substantially constant from the level immediately after injection. Even at the 1, 2 and 24-hour intervals, the level of $^{111}$In-desferrioxamine does not substantially increase in the brain, thymus, skeletal muscle, testis and salivary glands. This data is consistent with minimal delivery/uptake of the $^{111}$In-desferrioxamine by the brain, thymus, skeletal muscle, testis and salivary glands.

Figure 17:
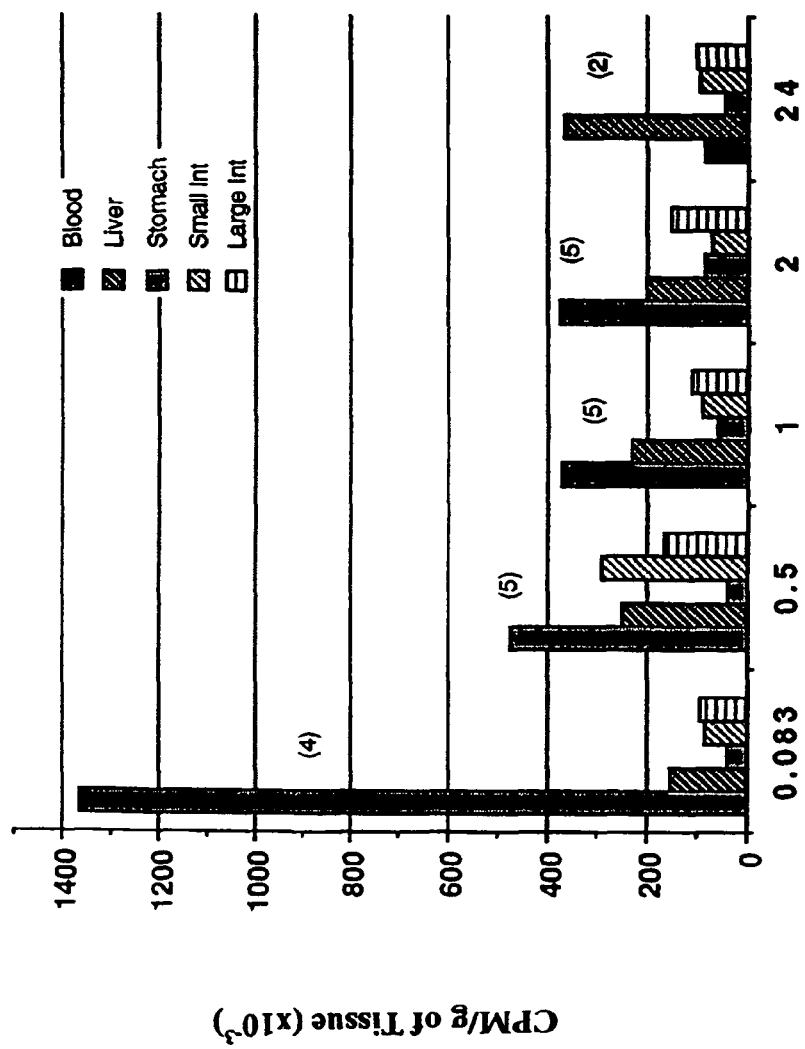
FIG. 17 is an another bar graph showing counts per minute/gram of tissue versus time in selected tissues or organs including blood, liver, stomach, small intestine and large intestine, in accordance with certain examples.

Referring specifically now to FIG. 17, at 24 hours following injection of $^{111}$In-desferrioxamine liposomes, the level of $^{111}$In-desferrioxamine is highest in the liver with smaller amounts found in the blood, stomach, small intestine and large intestine. This data is consistent with prolonged delivery of the $^{111}$In-desferrioxamine to the liver.

Figure 18:
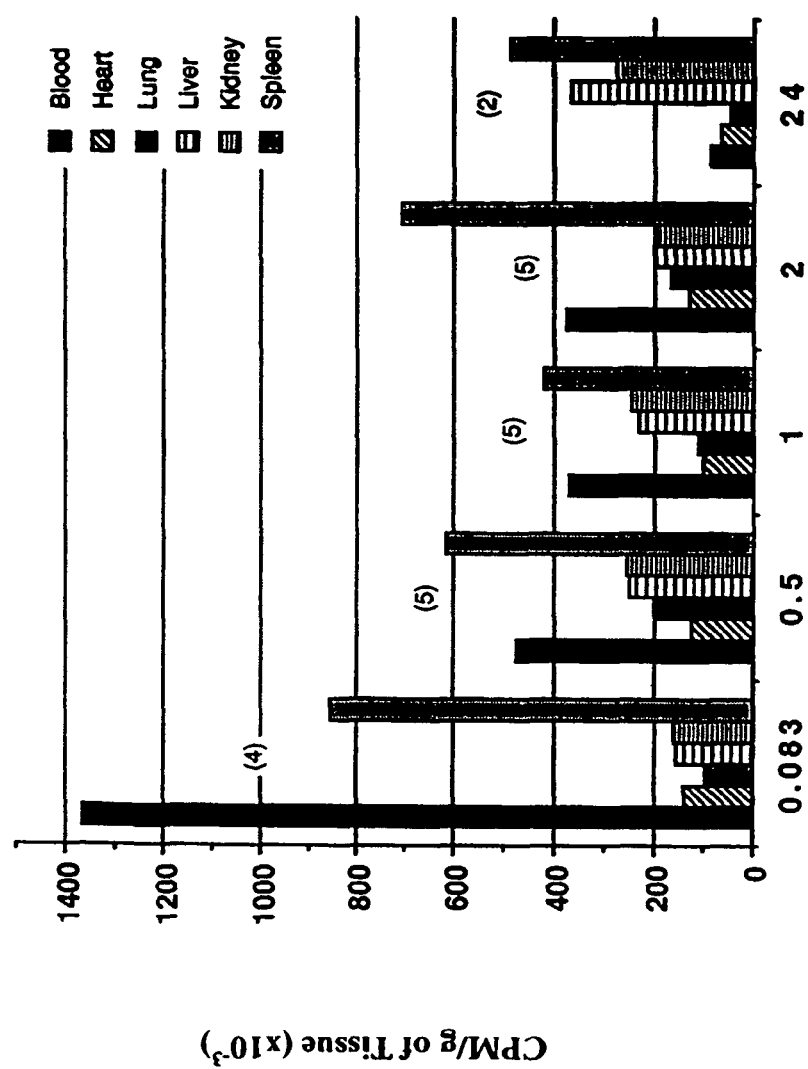
FIG. 18 is an additional bar graph showing counts per minute/gram of tissue versus time in selected tissues or organs including blood, heart, lung, liver, kidney and spleen, in accordance with certain examples.

Referring specifically now to FIG. 18, at 0.5 hours following injection of $^{111}$In-desferrioxamine, the level of $^{111}$In-desferrioxamine has decreased in the blood and increased in the lung, liver, kidney and spleen. At 24 hours following injection, the level of $^{111}$In-desferrioxamine is highest in the spleen and liver, with lesser amounts found in the kidney, blood, heart and lung. This data is consistent with prolonged delivery of the $^{111}$In-desferrioxamine to the liver and spleen.

Figure 19:
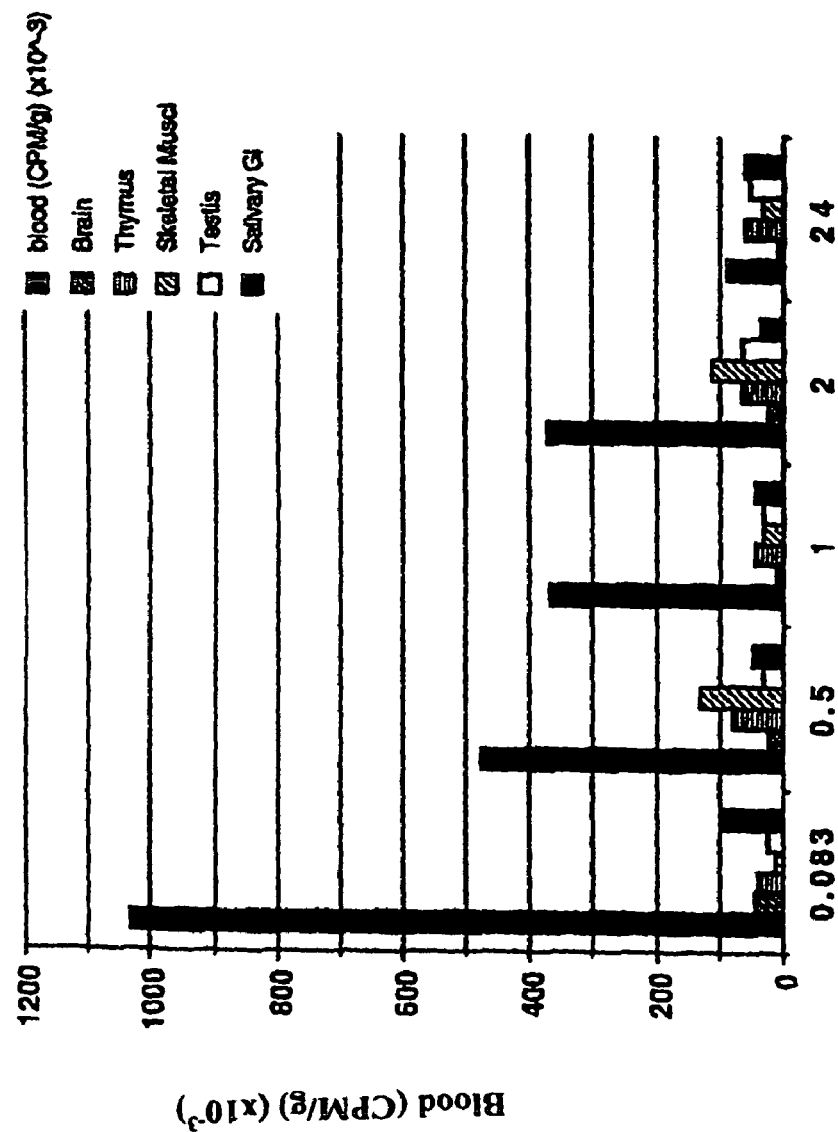
FIG. 19 is another bar graph showing counts per minute/gram of tissue versus time in selected tissues or organs including blood, brain, thymus, skeletal muscle, testis, and salivary glands, in accordance with certain examples.

Referring specifically now to FIG. 19, at 24 hours following injection of $^{111}$In-desferrioxamine, the level of $^{111}$In-desferrioxamine in the blood has decreased 10-fold. The levels of $^{111}$In-desferrioxamine in the brain has remained substantially constant. The levels of $^{111}$In-desferrioxamine in the thymus, skeletal muscle, testis and salivary glands has also decreased. This data is consistent with the limited ability of the $^{111}$In-desferrioxamine liposomes to cross the blood-brain barrier and is also consistent with a reduced uptake of the $^{111}$In-desferrioxamine by the thymus, skeletal muscle, testis and salivary glands.

Figure 20:
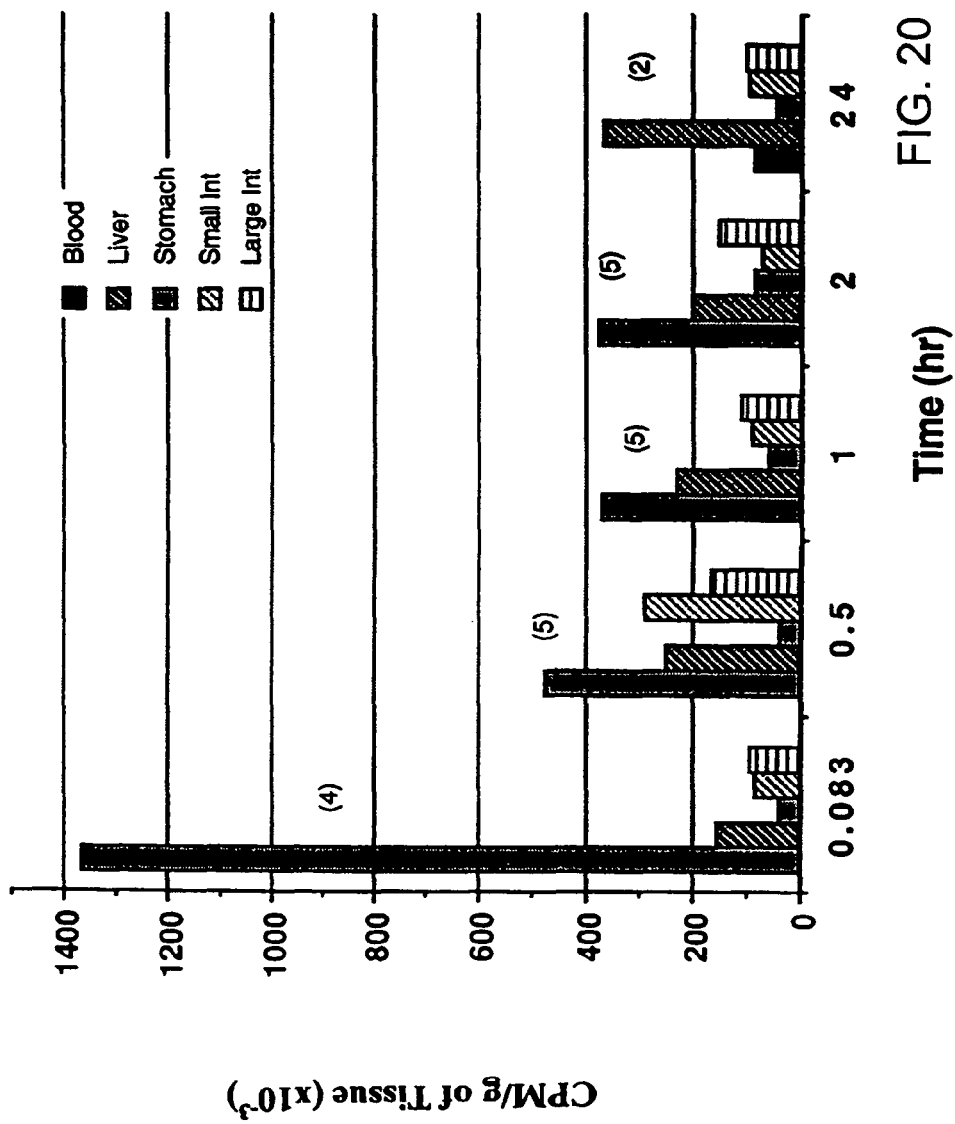
FIG. 20 is an additional bar graph showing counts per minute/gram of tissue versus time in selected tissues or organs including blood, liver, stomach, small intestine and large intestine, in accordance with certain examples.

Referring specifically now to FIG. 20, at 24 hours following injection of $^{111}$In-desferrioxamine liposomes, the level of $^{111}$In-desferrioxamine is highest in the liver. The level of $^{111}$In-desferrioxamine in the blood has decreased over 3-fold from the level at 0.5 hours following injection. The level of $^{111}$In-desferrioxamine in the stomach remained substantially constant over the 24 hour period. The level of $^{111}$In-desferrioxamine in the small intestine and the large intestine increased after 0.5 hours following injection, but leveled off at 1 hour following injection and remained substantially constant thereafter. This data is consistent with prolonged delivery of the $^{111}$In-desferrioxamine to the liver.

Figure 21:
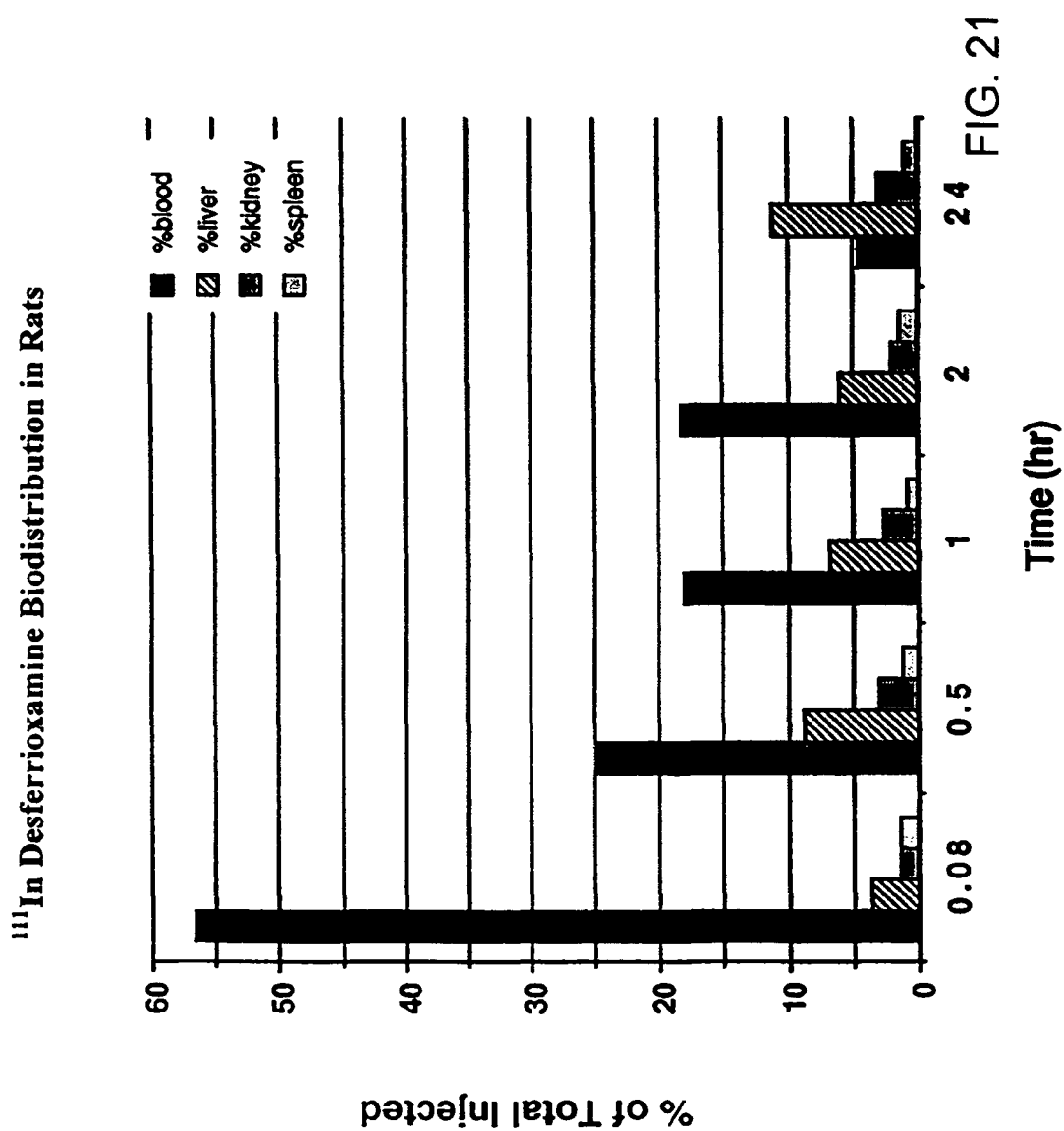
FIG. 21 is another bar graph showing percentage of total injected $^{111}$In-desferrioxamine versus time for selected organs including blood, liver, kidney and spleen, in accordance with certain examples.

Referring specifically now to FIG. 21, at 0.08 hours following injection, the largest percentage of the injected $^{111}$In-desferrioxamine is found in the blood (about 57%). Small percentages are also found in the liver (about 4%), kidney (about 2%) and spleen (about 2%). At 0.5 hours following injection, the percentage of $^{111}$In-desferrioxamine in the blood has decreased to about 25%, while the levels in the liver and kidney have increased to about 9% and about 3%, respectively. The level of $^{111}$In-desferrioxamine in the spleen has remained substantially constant at about 2%. At 24 hours following injection, the level in the blood has decreased to about 4%, while the level in the liver has increased to about 12%. This data is consistent with prolonged delivery of the $^{111}$In-desferrioxamine to the liver.

Figure 22:
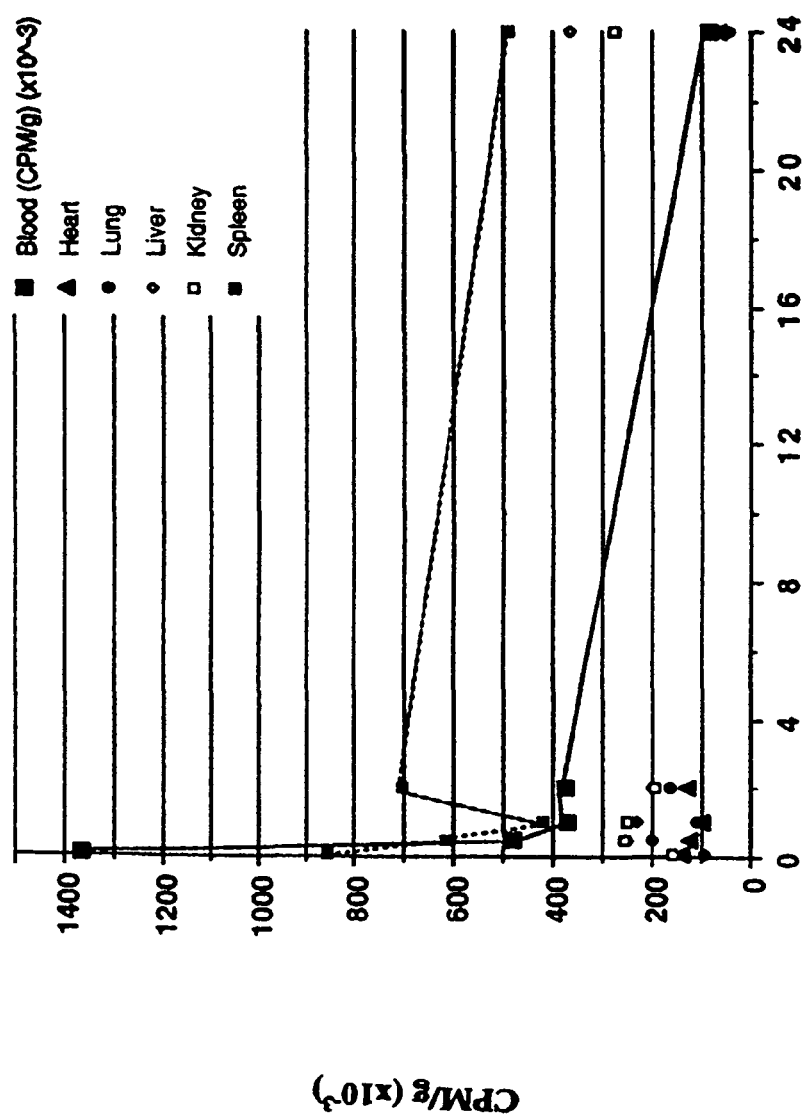
FIG. 22 is a graph showing counts per minute/gram of tissue versus time for selected tissues including blood, heart, lung, liver, kidney and spleen, in accordance with certain examples.

Referring specifically now to FIG. 22, following injection of $^{111}$In-desferrioxamine liposomes, the level is highest in the blood. Over the 24 hour period, the level declines in all tissues or organs, with highest levels found in the blood, liver, kidney and spleen. This data is consistent with prolonged delivery of the $^{111}$In-desferrioxamine to the liver and spleen.

Figure 23:
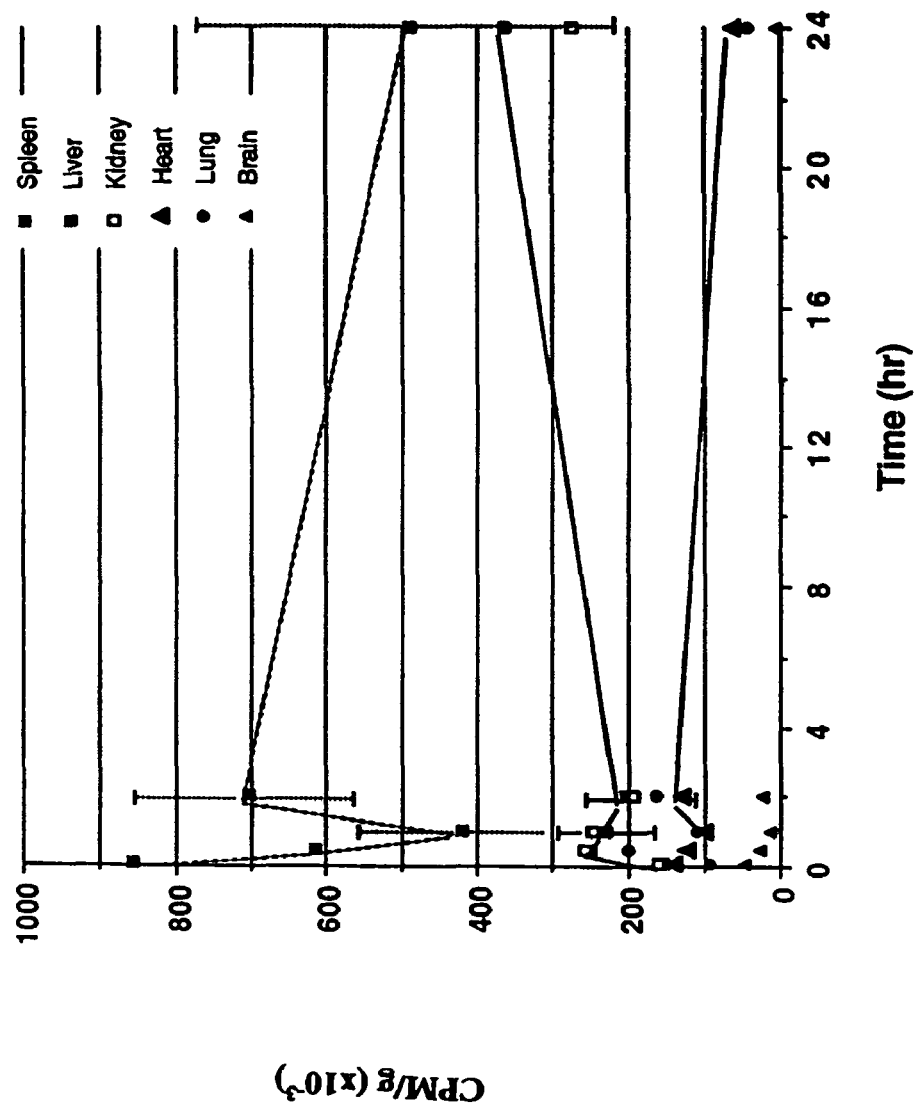
FIG. 23 is a graph showing counts per minute/gram of tissue versus time for selected tissues including spleen, liver, kidney, heart, lung, and brain, in accordance with certain examples.

Referring specifically now to FIG. 23, the level of $^{111}$In-desferrioxamine in the brain remains substantially constant over the 24 hour period. The levels of $^{111}$In-desferrioxamine in the blood decreases over the 24 hour period, while the levels of $^{111}$In-desferrioxamine in the liver and kidney increase over the 24 hour period. This data again is consistent with minimal crossing of the blood brain barrier by the $^{111}$In-desferrioxamine liposomes.

Figure 24:
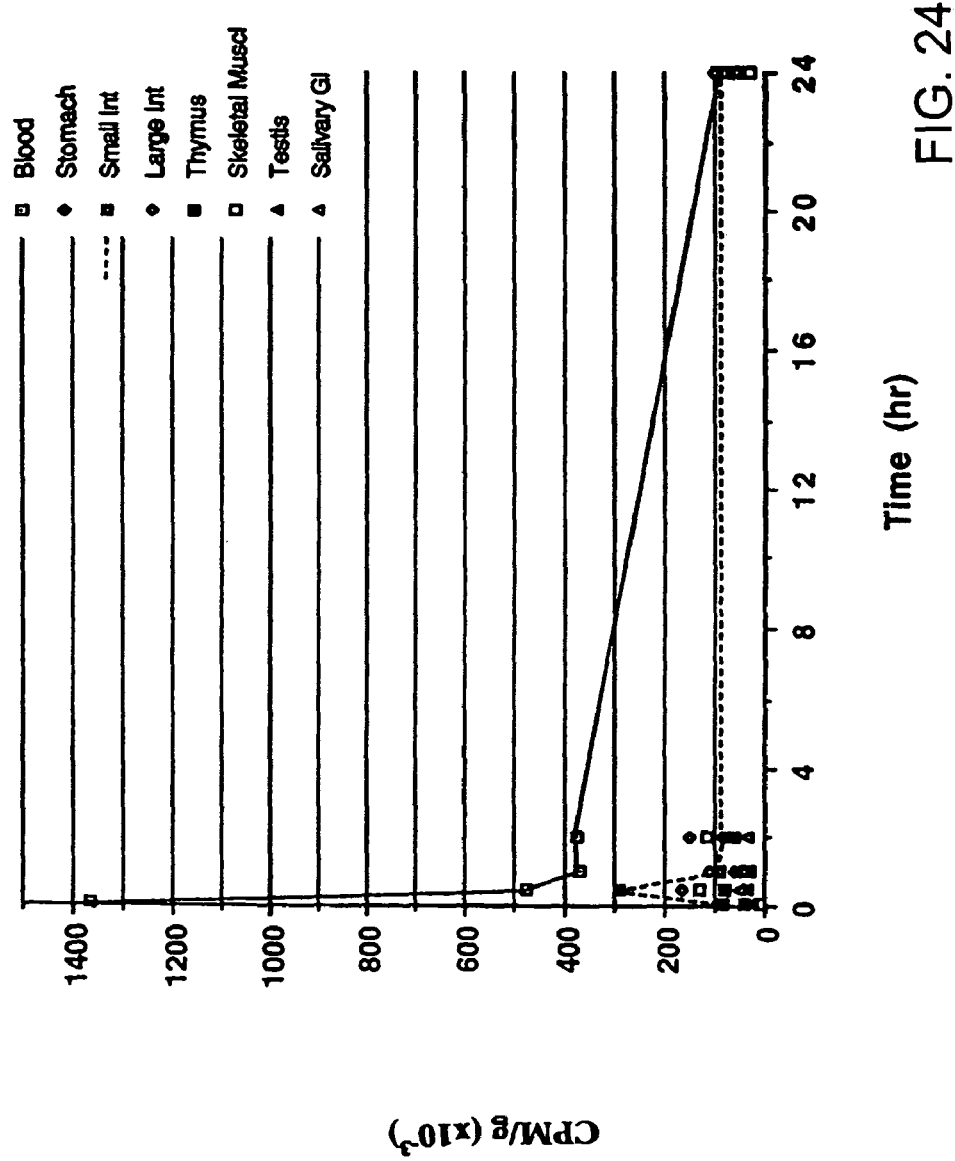
FIG. 24 is a graph showing counts per minute/gram of tissue versus time for selected tissues including blood, stomach, small intestine, large intestine, thymus, skeletal muscle, testis and salivary glands, in accordance with certain examples.

Referring specifically now to FIG. 24, at 24 hours following injection of $^{111}$In-desferrioxamine liposomes, the level in the blood, stomach, small intestine, large intestine, thymus, skeletal muscle, testis and salivary glands have dropped to substantially the same level. This data is consistent with minimal delivery and/or retention of the $^{111}$In-desferrioxamine by these tissues and organs.

Figure 25:
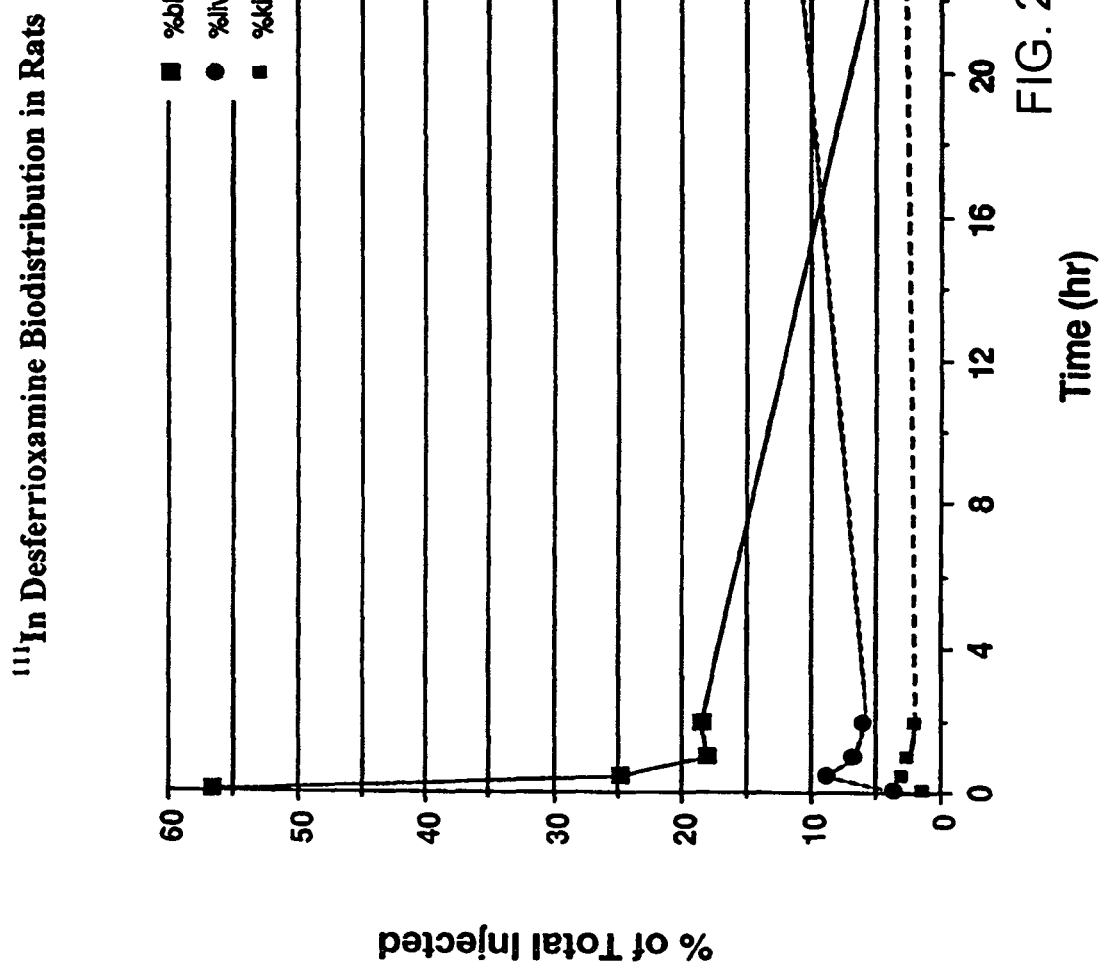
FIG. 25 is a graph showing percentage of total injected $^{111}$In-desferrioxamine versus time for selected tissues or organs including blood, liver and kidney, in accordance with certain examples.
Figure 26:
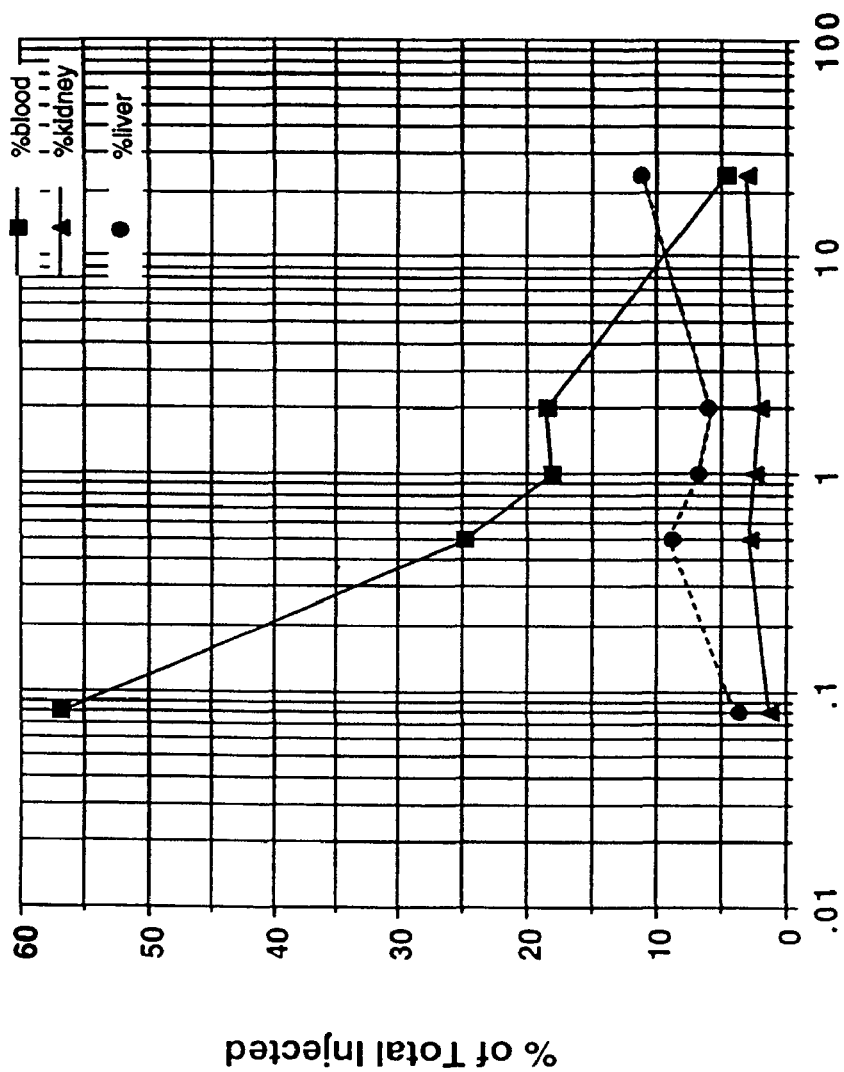
FIG. 26 is a graph showing percentage of total injected $^{111}$In-desferrioxamine versus time (logarithmic scale) for selected tissues or organs including blood, liver, and kidney, in accordance with certain examples.

Referring specifically now to FIGS. 25 and 26, at 24 hours following injection of $^{111}$In-desferrioxamine liposomes, the percentage of $^{111}$In-desferrioxamine in the blood has decreased from about 58% to about 4%. The percentage of $^{111}$In-desferrioxamine in the liver has increased from about 4% to about 12%. The percentage of $^{111}$In-desferrioxamine in the kidney has increased slightly from about 2% to about 3%. This data is consistent with prolonged delivery of the $^{111}$In-desferrioxamine to the liver.

Figure 27:
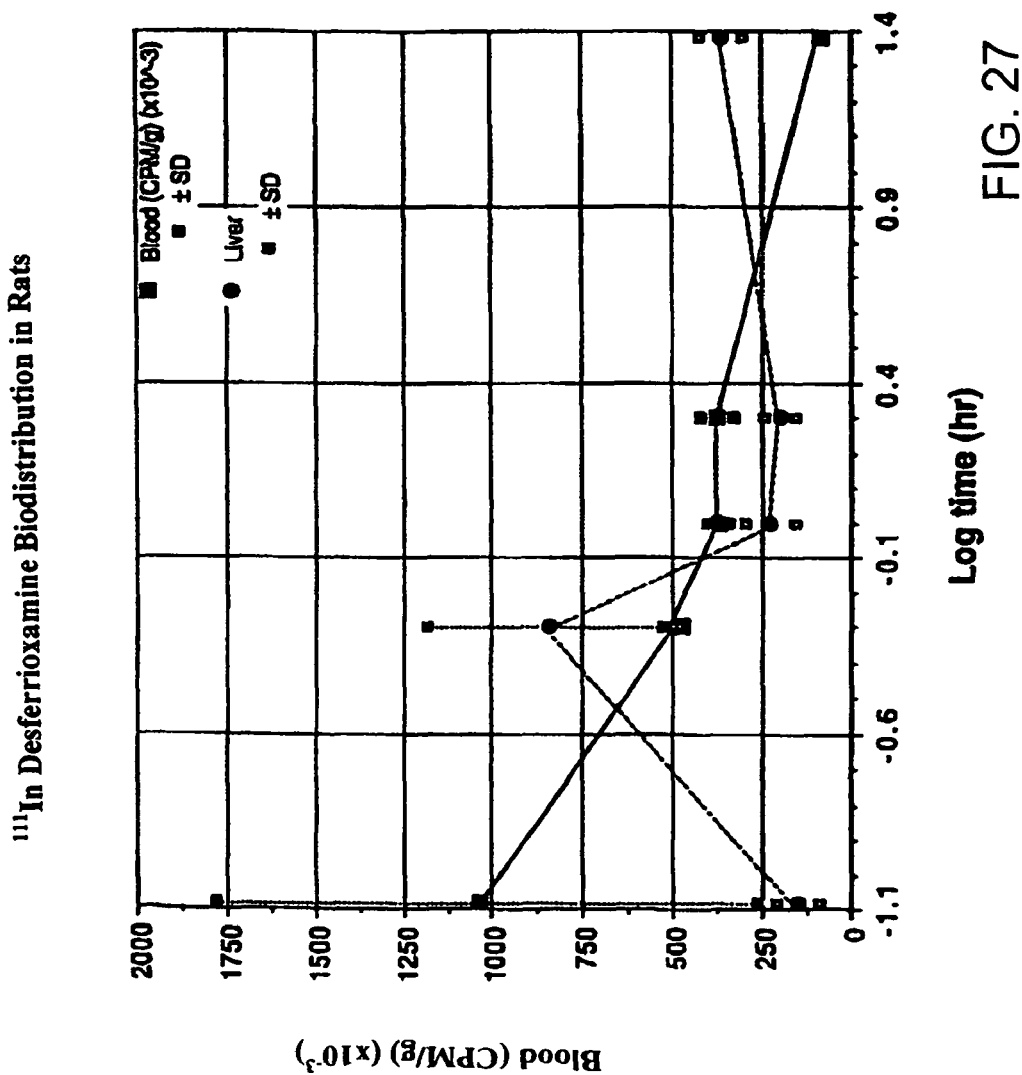
FIG. 27 is a bar graph showing counts per minute versus log time for selected tissues or organs including blood and liver, in accordance with certain examples.

Referring specifically now to FIG. 27, the level of $^{111}$In-desferrioxamine in the blood decreases about 10-fold over the 24 hour period following injection. The level of $^{111}$In-desferrioxamine in the liver increases about 2-fold over the 24 hour period. This data is consistent with prolonged delivery of the $^{111}$In-desferrioxamine to the liver.

Example 19

Targeted Mannosylated and Cationic Liposomes

Plain liposomes, mannosylated liposomes and cationic liposomes were prepared and studied for their effect on targeting the heart and liver.

Plain liposomes were prepared as follows: 3.4 mg cholesterol was dissolved in 3 mL chloroform in a round-bottom flask. 15.96 mg of phosphatidylcholine was added to the above solution, followed by the addition of 195 ug of Rh-DOPE, commercially available from Avanti Lipids, (Molar ratio PC/Chol/Rh-DOPE=7:3:0.005). The solution was vortexed thoroughly, and dried on a rotary evaporator for 30 minutes at 40° C. to form a film. The film was hydrated with 3 mL PBS and sonicated to form liposomes. The resulting suspension was passed 10× through 0.45 um Millipore discs, and 10× through 0.22 um Millipore discs. Liposomes were stored at 4° C. until used.

Mannosylated liposomes were prepared as follows: 2.316 mg cholesterol was dissolved in 3 mL chloroform in a round-bottom flask. 15.96 mg of phosphatidylcholine and 0.8 mg para-aminophenyl-alpha-D-mannopyranoside were added to the above solution, followed by the addition of 195 ug of Rh-DOPE. (Molar ratio PC/Chol/mannopyranoside/Rh-DOPE=7:2:1:0.005). The resulting solution was vortexed thoroughly, and dried on a rotary evaporator for 30 minutes at 40° C. to form a film. The film was hydrated with 3 mL PBS, sonicated to form liposomes. The suspension was passed 10× through 0.45 um Millipore discs, and 10× through 0.22 um Millipore discs. The liposomes were stored at 4° C. until used.

Cationic liposomes were prepared as follows: 2.316 mg cholesterol was dissolved in 3 mL chloroform in a round-bottom flask. 10.64 mg of phosphatidylcholine and 6.98 mg DOTAP were added to the above solution, followed by the addition of 195 ug of Rh-DOPE. (Molar ratio PC/Chol/DOTAP/Rh-DOPE=7:3:5:0.005). The resulting solution was vortexed thoroughly, and dried on a rotary evaporator for 30 minutes at 40° C. to form a film. The film was hydrated with 3 mL PBS, sonicated to form liposomes. The suspension was passed 10× through 0.45 um Millipore discs, and 10× through 0.22 um Millipore discs. Liposomes were saved at 4° C. until used.

100 uL of the liposomes were separately injected into two mice in the following order:
1. Plain liposomes were injected into mouse #1 and #2.
2. Mannosylated liposomes were injected into mouse #3 and #4.
3. Cationic Liposomes were given to mouse #5 and #6.

Animals were sacrificed 20 minutes after injection by pentobarbitol overdose. Livers and hearts were collected and stored at −20° C. until used for cryosectioning. Cryosections were made on each organ and rhodamine fluorescence intensity was evaluated on each section.

Figure 28:
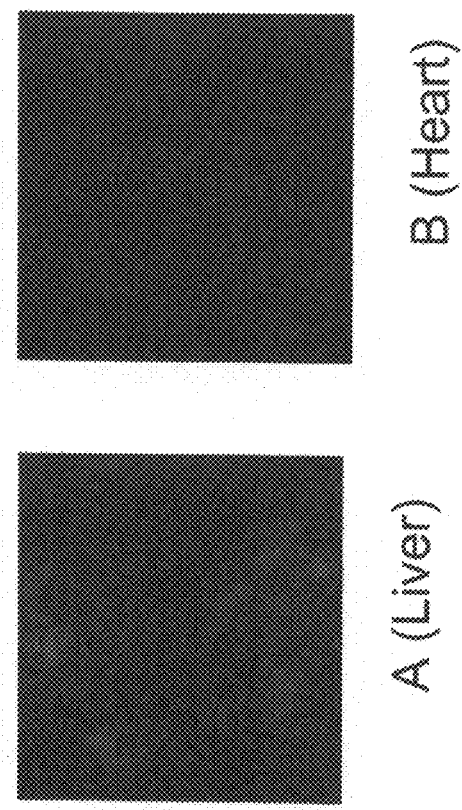
FIGS. 28A and 28B are fluorescence micrographs showing plain liposome distribution in the heart and liver, in accordance with certain examples.

Referring to FIGS. 28A and 28B, when plain liposomes were used the mean fluorescence intensity in the liver was measured as 222±22.86 (FIG. 28A), and the mean fluorescence intensity in the heart was measured as 106±6.52 (FIG. 28B). These results were consistent with localization of plain liposomes about 2× more in the liver than in the heart.

When mannosylated liposomes were used (FIGS. 29A and 29B), the mean fluorescence intensity in the liver was measured as 252.97±8.86 (FIG. 29A), and the mean fluorescence intensity in the heart was measured as 106±6.52 (FIG. 29B). These results were consistent with increased uptake in mannosylated liposomes in the liver, as compared to plain liposome uptake, and little or no uptake differential in the heart, when comparing plain and mannosylated liposome uptake.

When cationic liposomes were used, the mean fluorescence intensity in the liver was measured as 245.87±14.47 (FIG. 30A), and the mean fluorescence intensity in the heart was measured as 244.65±27.18 (FIG. 30B). These results were consistent with about 10% more cationic liposomes taken up by the liver (FIG. 30A) as compared to the level of plain liposomes taken up by the liver (FIG. 28A). These results were also consistent with about 110% more cationic liposomes taken up by the heart (FIG. 30B) as compared to the level of plain liposomes taken up by the heart (FIG. 28B).

Figure 31:
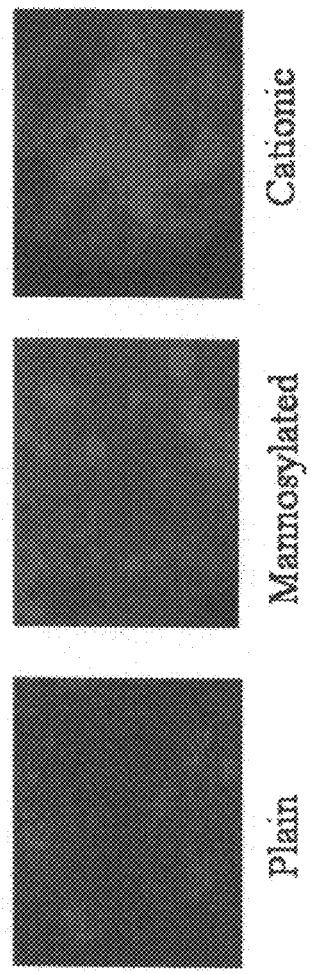
FIG. 31 are fluorescence micrographs showing distribution of plain, mannosylated and cationic liposomes in the liver, in accordance with certain examples.
Figure 32:
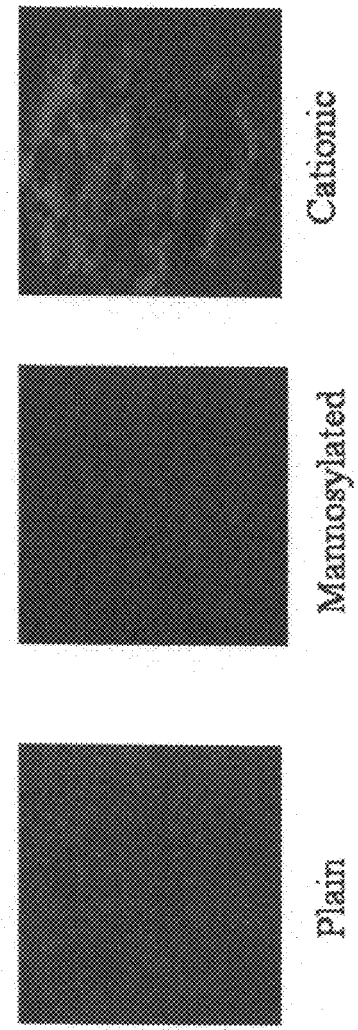
FIG. 32 are fluorescence micrographs showing distribution of plain, mannosylated and cationic liposomes in the heart, in accordance with certain examples.

In summary, mannosylated liposomes were found to localize very high in the liver (FIG. 31), whereas cationic liposomes were found to localize very high in the heart (FIG. 32), as compared to the levels of plain liposomes taken up by each respective organ.

Although the targeted iron chelator delivery systems have been described above in terms of certain illustrative aspects and examples, the person of ordinary skill in the art will recognize, given the benefit of this disclosure, that many equivalents, alterations, substitutions, modifications and the like to the specific aspects and examples described herein are possible. Should the meaning of any of the terms of any of the patents or other citations incorporated by reference conflict with the meaning of any of the terms used herein, the meaning of the terms used in this disclosure are intended to be controlling. When introducing elements of the examples disclosed herein and in the claims below, the articles "a", "an", "the" and "said" are intended to mean that there are one or more of the elements. The terms "comprising", "including" and "having" are intended to be open ended and mean that there may be additional elements other than the listed elements.

What is claimed is:

1. A targeted iron chelator delivery system for targeting the heart or liver, the targeted iron chelator delivery system comprising:
an iron chelator; and
a lipid carrier comprising:
a targeting agent for targeting the heart or liver,
a phosphatidylcholine,
a cholesterol,
a phosphatidylethanolamine, and
one or more cationic lipids, wherein the one or more cationic lipids are present in an amount effective to selectively increase uptake of the targeted iron chelator delivery system by the heart or liver.

2. The targeted iron chelator delivery system of claim 1, wherein the iron chelator is selected from the group consisting of desferrioxamine, deferiprone, PIH, rhodotorulic acid, HBED, HBPD, 2,3-dihydroxybenzoic acid, DTPA, and an iron chelator produced by a bacterial siderophore.

3. The targeted iron chelator delivery system of claim 1, wherein the lipid carrier is a vesicle.

4. The targeted iron chelator delivery system of claim 3, wherein the vesicle is multilamellar or unilamellar.

5. The targeted iron chelator system of claim 3, wherein the cross-sectional diameter of the vesicle is about 10 nm to about 10 μm.

6. The targeted iron chelator system of claim 3, wherein the iron chelator is encapsulated between a vesicle bilayer or intercalated within the vesicle bilayer.

7. The targeted iron chelator system of claim 3, wherein the iron chelator is encapsulated within a central cavity of the vesicle.

8. The targeted iron chelator system of claim 1, wherein the iron chelator is present in a therapeutic amount.

9. The targeted iron chelator system of claim 1, wherein the targeting agent is an antibody specific for a cardiac protein selected from the group consisting of a cardiac myocyte protein, a vasculature protein, and a matrix protein.

10. The targeted iron chelator system of claim 1, wherein the targeted iron chelator delivery system is configured for oral administration, rectal administration, subcutaneous administration, intravenous or arterial infusion or injection, suppository administration, or nasal administration.

11. The targeted iron chelator system of claim 1, wherein the targeted iron chelator drug delivery system is dissolved in a pharmaceutically acceptable carrier.

12. The targeted iron chelator system of claim 1, wherein the lipid carrier is further tagged with a label selected from the group consisting of a fluorescent label, a colorimetric label, a magnetically active label, and a radioactive label.

13. A targeted iron chelator delivery system for targeting the heart or liver, the targeted iron chelator delivery system comprising:
   an iron chelator; and
   a lipid carrier comprising:
      a phosphatidylcholine,
      cholesterol,
      a phosphatidylethanolamine, and
      one or more cationic lipids, wherein the one or more cationic lipids are present in an amount effective to selectively increase uptake of the targeted iron chelator delivery system by the heart or liver; and wherein the lipid carrier is further tagged with a label.

14. A system comprising
   a liposome and
   an iron chelator within the liposome, the liposome further comprising:
      a cholesterol,
      a phosphatidycholine,
      a phosphatidylethanolamine, and
      one or more cationic lipids, wherein the one or more cationic lipids are present in an amount effective to selectively increase uptake of the system by the heart or liver, wherein the iron chelator is selected from the group consisting of desferrioxamine, deferiprone, PIH, rhodotorulic acid, HBED, HBPD, 2,3-dihydroxybenzoic acid, DTPA, and an iron chelator produced by a bacterial siderophore, and wherein the liposome is further tagged with a label.

15. The system of claim 14, wherein the liposome further comprises an antibody specific for a cardiac protein selected from the group consisting of a cardiac myocyte protein, a vasculature protein and a matrix protein.

16. The system of claim 14, wherein the one or more cationic lipids is provided by DOTAP.

17. A targeted iron chelator delivery system for targeting the heart, the targeted iron chelator delivery system comprising:
   an iron chelator; and
   a lipid carrier comprising:
      a phosphatidylcholine,
      a cholesterol,
      and
      one or more cationic lipids provided by the presence of DOTAP, wherein the one or more cationic lipids are present in an amount effective to increase uptake of the targeted iron chelator delivery system by the heart by 110% as compared to plain liposomes, wherein the plain liposomes lack DOTAP, and wherein the ratio of phosphatidylcholine:cholesterol:DOTAP is 7:3:5.

* * * * *